US006172038B1

(12) United States Patent
Shai et al.

(10) Patent No.: US 6,172,038 B1
(45) Date of Patent: Jan. 9, 2001

(54) ANTIPATHOGENIC PEPTIDES AND COMPOSITIONS COMPRISING THEM

(75) Inventors: Yechiel Shai, Yahud; Ziv Oren, Rishon Le-Zion, both of (IL)

(73) Assignee: Yeda Research and Development Co. LTD, Rehovot (IL)

( * ) Notice: Under 35 U.S.C. 154(b), the term of this patent shall be extended for 0 days.

(21) Appl. No.: 09/125,605

(22) PCT Filed: Feb. 20, 1997

(86) PCT No.: PCT/IL97/00066

§ 371 Date: Dec. 8, 1998

§ 102(e) Date: Dec. 8, 1998

(87) PCT Pub. No.: WO97/31019

PCT Pub. Date: Aug. 28, 1997

(30) Foreign Application Priority Data

Feb. 22, 1996 (IL) ..................................................... 117223

(51) Int. Cl.[7] .......................... A61K 38/02; A61K 38/10; A61K 38/16; C07K 7/08; C07K 14/00

(52) U.S. Cl. .................................. 514/2; 514/12; 514/13; 514/14; 514/21; 530/300; 530/324; 530/326; 530/327; 530/345

(58) Field of Search .................................... 514/2, 12, 13, 514/14, 15; 530/300, 324, 325, 326, 327, 345

(56) References Cited

U.S. PATENT DOCUMENTS 5,373,053 * 12/1994 Berg et al. .......................... 525/54.1

OTHER PUBLICATIONS

Wade, D., et al., "Antibacterial Peptides Designed as Analogs or Hybrids of Cecropins and Melittin," *International Journal of Peptide & Protein Research* 40:429–436 (1992).

Boman, H.G., et al., "Antibacterial and Antimalarial Properties of Peptides That are Cecropin–Melittin Hybrids," *FEBS Letters* 259–1:103–106 (1989).

Rapaport, D., et al., "pH– and Ionic Strength–Dependent Fusion of Phospholipid Vesicles Induced by Pardaxin Analogues or by Mixtures of Charge–Reversed Peptides," *Biochemistry* 32:3291–3297 (1993).

Pouny, Y., et al., "Interaction of D–Amino Acid Incorporated Analogues of Pardaxin with Membranes," *Biochemistry* 31:9482–9489 (1992).

Shai, Y., et al., "Diastereomers of Cytolysins, a Novel Class of Potent Antibacterial Peptides," *The Journal of Biological Chemistry* 271–13:7305–7308 (1996).

Agawa, Y., et al., "Interaction with Phospholipid Bilayers, Ion Channel Formation, and Antimicrobial Activity of Basic Amphioathic α–Helical Model Peptides of Various Chain Lengths," *The Journal of Biological Chemistry* 266–30:20218–20222 (1991).

(List continued on next page.)

*Primary Examiner*—Jeffrey E. Russel
(74) *Attorney, Agent, or Firm*—Browdy and Neimark

(57) ABSTRACT

Peptides which have a net positive charge and none or only a partial a-helix configuration were found to have a non-hemolytic selective cytolytic activity. The peptides may be derived from natural peptides such as pardaxin and mellitin and fragments thereof in which L-amino acid residues are replaced by corresponding D-amino acid residues, and cyclic derivatives of the foregoing, or are diastereomers of linear peptides composed of varying ratios of at least one positively charged amino acid and at least one hydrophobic amino acid, and in which at least one of the amino acid residues is a D-amino acid, and preferably at least one third of the sequence is composed of D-amino acid residues. Pharmaceutical compositions comprising the non-hemolytic cytolytic peptides can be used for the treatment of several diseases caused by pathogens including antibacterial, fungal, viral, mycoplasma and protozoan infections and for the treatment of cancer.

15 Claims, 14 Drawing Sheets

OTHER PUBLICATIONS

Altenbach, C., et al., "The Aggregation State of Spin–Labeled Melittin in Solution and Bound to Phospholipid Membranes: Evidence That Membrane–Bound Melittin is Monomeric," *Proteins: Structure, Function, and Genetics* 3:230–242 (1988).

Anderson, D., et al., "Melittin Forms Crystals Which are Suitable for High Resolution X–ray Structural Analysis and Which Reveal a Molecular 2–Fold Axix of Symmetry," *The Journal of Biological Chemistry* 255–6:2578–2582 (1980).

Anzai, K., et al., "Formation of ion Channels in Planar Lipid Bilayer Membranes by Synthetic Basic Peptides," *Biochimica et Biophysica Acta* 1064:256–266 (1991).

Bartlett, G.R., "Phosphorus Assay in Column Chromatography," *The Journal of Biological Chemistry* 234:466–468 (1959).

Batenburg, A.M., et al., "Lipid Specific Penetration of Melittin into Phospholipid Model Membranes," *Biochimica et Biophysica Acta* 903:155–165 (1987).

Batenburg, A.M., et al., "Melittin–Induced Changes of the Macroscopic Structure of Phosphatidylethanolamines" *Biochemistry* 27:2324–2331 (1988).

Batenburg, A.M., et al., "Interaction of Melittin with Negatively Charged Phospholipids: Consequences for Lipid Organization," *FEBS Letters* 223–1:148–154 (1987).

Bazzo, R., et al., "The Structure of Melittin, A $^1$H–NMR Study in Methanol," *Eur. J. Biochem.* 173:139–146 (1988).

Benkirane, N., et al., "Antigenicity and ,mmunogenicity of Modified Synthetic Peptides Containing D–Amino Acid Residues, Antibodies to A D–Enantiomer Do Recognize the Parent L–Hexapeptide and Reciprocally," *The Journal of Biological Chemistry* 268–35:26279–26285 (1993).

Beschiaschvili, G., et al., "Melittin Binding to Mixed Phosphatidylglycerol/Phosphatidylcholine Membranes," *Biochemistry* 29:52–58 (1990).

Bessalle, R., et al., "All D–magainin: Chirality, Antimicrobial Activity and Proteolytic Resistance," *FEBS Letters* 274–1,2:151–155 (1990).

Bolen, E.J., et al., "Quenching of Tryptophan Fluorescence by Brominated Phospholipid," *Biochemistry* 29:9638–9643 (1990).

Boman, H.G., "Peptide Antibiotics and Their Role in Innate Immunity," *Annu. Rev. Immunol.* 13:61–92 (1995).

Chen, H.C., et al., "Synthetic Magainin Analogues with Improved Antimicrobial Activity," *FEBS Letters* 236–2:462–466 (1988).

Cornut, I., et al., "The Amphipathic α–Helix Concept, Application to the De Novo Design of Ideally Amphipathic Leu, Lys Peptides with Hemolytic Activity Higher Than That of Melittin," *FEBS Letters* 349:29–33 (1994).

Dempsey, C.E., "The Actions of Melittin on Membranes," *Biochimica et Biophysica Acta* 1031:143–161 (1990).

Dhople, V.M., et al., "δ–Toxin, Unlike Melittin, Has Only Hemolytic Activity and no Antimicrobial Activity: Rationalization of This Specific Biological Activity," *Bioscience Reports* 13–4:245–250 (1993).

Eisenberg, D., et al., "Analysis of Membrane and Surface Protein Sequences with the Hydrophic Moment Plot," *J. Mol. Biol.* 179:125–142 (1984).

Fisher, P.J., et al., "Calmodulin Interacts with Amphiphilic Peptides Composed of all D–Amino Acids," *Nature* 368:651–653 (1994).

Gazit, E., "Mode of Action of the Antibacterial Cecropin B2: A Spectrofluorometric Study," *Biochemistry* 33:10681–10692 (1994).

Greenfiled, N., et al., "Computed Circular Dichroism Spectra for the Evaluation of Protein Conformation," *Biochemistry* 8:4108–4116 (1969).

Habermann, V.E., et al., "Sequenzanalyse des Melittins aus den Tryptischen und Peptischen Spaltstucken," *Hoppe–Seyler's Z. Physiol. Chem.* 348:37–50 (1967).

Katchalski, E., et al., "Synthesis and Chemical Properties of Poly–α–Amino Acids," *Adv. Protein Chem.* 13:243–492 (1958).

Kuchinka, E., et al., "Interaction of Melittin with Phosphatidylcholine Membranes. Binding Isotherm and Lipid Head–Group Conformation," *Biochemistry* 28:4216–4221 (1989).

Li, Z.Q., et al., "Effects on Electrophoretic Mobility and Antibacterial Spectrum of Removal of Two Residues from Synthetic Sarcotoxin IA and Addition of the Same Residues to Cecropin B," *FEBS Letters* 231–2:299–302 (1988).

Loew, L.M., et al., "Diffusion Potential Cascade. Convenient Detection of Transferable Membrane Pores," *Biochemistry* 22:837–844 (1983).

Merrifield, R.B., et al., "Synthesis of the Antibacterial Peptide Cecropin A(1–33)," *Biochemistry* 21:5020–5031 (1982).

Mor, A., et al., "Isolation, Amino Acid Sequence, and Synthesis of Dermaseptin, a Novel Antimicrobial Peptide of Amphibian Skin," *Biochemistry* 30:8824–8830 (1991).

Okada, M., et al., "Mode of Action of a Bacterial Protein Induced in the Haemolymph of *Sarcophaga peregrina* (flesh–fly) Larvae," *Biochem. J.* 222:119–124 (1984).

Oren, Z., et al., "A Class of Highly Potent Antibacterial Peptides Derived from Pardaxin, a Pore–forming Peptide Isolated from Moses sole fish *Pardachirus marmoratus,*" *Eur. J. Biochem.* 237:303–310 (1996).

Papahadjopoulos, D., et al., "Phospholipid Model Membranes. Structureal Characteristics of Hydrated Liquid Crystals," *Biochimica et Biophysica Acta* 135:624–638 (1967).

Perez, P.E., et al., "Determination of the Secondary Structure of Selected Melittin Analogues with Different Haemolytic Activities," *Biochem. J.* 299:587–591 (1994).

Rapaport, D., et al., "Aggregation and Organization of Pardaxin in Phospholipid Membranes. A Fluorescence Energy Transfer Study," *The Journal of Biological Chemistry* 267–10:6502–6509 (1992).

Rapaport, D., et al., "Interaction of Fluorescently Labeled Pardaxin and Its Analogues with Lipid Bilayers," *The Journal of Biological Chemistry* 266–35:23769–23775 (1991).

Rizzo, V., et al., "Alamethicin Incorporation in Lipid Bilayers: A Thermodynamic Study," *Biochemistry* 26:2751–2759 (1987).

Russell, P.E., et. al., "Fifty Years of Antimicrobials: Past Perspectives and Future Trends," Cambridge University Press 67–85 (1995).

Schwarz, G., et al., "Incorporation Kinetics in a Membrane, Studied with the Pore–Forming Peptide Alamethicin," *Biophys. J.* 52:685–692 (1987).

Segrest, J.P., et al., "Amphipathic Helix Motif: Classes and Properties," *Proteins:Structure, Function, and Genetics* 8:103–117 (1990).

Shai, Y., "Molecualr Recognition Between Membrane–Spanning Polypeptides," *TIBS* 20:460–464 (1995).

Shai, Y., "Pardaxin: Channel Formation by a Shark Repellant Peptide From Fish," *Toxicology* 87:109–129 (1994).

Shai, Y., et al., "Sequencing and Synthesis of Pardaxin, a Polypeptide from the Red Sea Moses Sole with Ionophore Activity," *FEBS Letters* 242–1:161–166 (1988).

Shai, Y., et al., "pH–Dependent Pore Formation Properties of Pardaxin Analogues," *The Journal of Biological Chemistry* 266–33:22346–22354 (1991).

Shaw, N., "Lipid Composition as a Guide to the Classification of Bacteria," *Adv. Appl. Microbiol.* 17:63–108 (1974).

Sims, P.J., et al., "Studies on the Mechanism by Which Cyanine Dyes Measure Membrane Potential in Red Blood Cells and Phosphatidylcholine Vesicles," *Biochemistry* 13–16:3315–3330 (1974).

Steiner, H., et al., "Sequence and Specificity of Two Antibacterial Proteins Involved in Insect Immunity," *Nature* 292:246–248 (1981).

Terwilliger T.C., et al., "The Structure of Melittin. Structure Determination and Partial Refinement," *The Journal of Biological Chemistry* 257–11:6010–6015 (1982).

Terwilliger, T.C., et al., "The Structure of Melittin. Interpretation of the Structure," *The Journal of Biological Chemistry* 257–11:6016–6022 (1982).

Thompson, S.T., et al., "Melittin–Like Peptides from the Shark–Repelling Defense Secretion of the Sole *Pardachirus pavoninus,*" *Science* 233:341–343 (1986).

Verkleij, A.J., et al., "The Asymmetric Distribution of Phospholipids in the Human Red Cell Membrane. A Combined Study Using Phospholipases and Freeze–Etch Electron Membrane," *Biochimica et Biophysica Acta* 323:178–193 (1973).

Wade, D., et al., "All–D Amino Acid–Containing Channel–Forming Antibiotic Peptides," *Proc. Natl. Acad. Sci.* 87:4761–4765 (1990).

Wu, C.S., et al., "Ordered Conformation of Polypeptides and Proteins in Acidic Dodecyl Sulfate Solution," *Biochemistry* 20:566–570 (1981).

Zagorski, M.G., et al., "Solution Structure of Pardaxin P–2," *Biochemistry* 30:8009–8017 (1991).

Zaner, H., et al., "The Need for New Antibiotics: Possible Ways Forward" (not dated).

* cited by examiner

SEQUENCE LISTING

<160> NUMBER OF SEQ ID NOS: 2

<210> SEQ ID NO 1
<211> LENGTH: 33
<212> TYPE: PRT
<213> ORGANISM: Pardachirus marmoratus/pavoninus

<400> SEQUENCE: 1

```
Gly Phe Phe Ala Leu Ile Pro Lys Ile Ile Ser Ser Pro Leu Phe Lys
 1               5                  10                  15

Thr Leu Leu Ser Ala Val Gly Ser Ala Leu Ser Ser Ser Gly Gly Gln
            20                  25                  30

Glu
```

<210> SEQ ID NO 2
<211> LENGTH: 26
<212> TYPE: PRT
<213> ORGANISM: Apis mellifera

<400> SEQUENCE: 2

```
Gly Ile Gly Ala Val Leu Lys Val Leu Thr Thr Gly Leu Pro Ala Leu
 1               5                  10                  15

Ile Ser Trp Ile Lys Arg Lys Arg Gln Gln
            20                  25
```

ANTIPATHOGENIC PEPTIDES AND COMPOSITIONS COMPRISING THEM

FIELD OF THE INVENTION

The present invention concerns novel non-hemolytic cytolytic peptides, compositions comprising them and their use in the treatment of diseases or disorders and in agriculture.

BACKGROUND OF THE INVENTION

In the text below, reference is being made to prior art documents, the complete particulars of which can be found in the "References" section at the end of the specification before the claims.

The increasing resistance of microorganisms to the available antimicrobial drugs has resulted in extensive studies focused on developing alternative antimicrobial compounds.

In addition, or complementary, to the highly specific cell-mediated irmune response, vertebrates and other organisms have a defense system made up of distinct groups of broad spectrum cytolytic, e.g., antibacterial, peptides.

Studies on lipid-peptide interactions of such cytolytic peptides, also known as cytolysins, tend to emphasize the importance of the amphipathic α-helical structure for their cytolvtic activity. This conclusion is based mainly on studies with cytolysins that act on either mammalian cells or bacteria alone or on both types of cells. A major group of cytolytic peptides in this family are host-defense short linear peptides (≦40 amino acids), which are devoid of disulfide bridges (Boman, 1995). These peptides vary considerably in chain length, hydrophobicity and overall distribution of charges, but share a common structure upon association with lipid bilayers, namely, an amphipathic α-helix structure (Segrest et al., 1990).

Examples of known cytolysins include: (i) antibacterial peptides that are cytolytic to bacteria only, e.g. cecropins, isolated from the cecropia moth (Steiner et al., 1981), magainins (Zasloff, 1987) and dermaseptins (Mor et al., 1991) isolated from the skin of frogs; (ii) cytolysins that are selectively cytotoxic to mammalian cells, such as δ-hemolysin isolated from *Staphylococcus aureus* (Dhople and Nagaraj, 1993); and (iii) cytolysins that are not cell-selective, such as the bee venom melittin (Habermann and Jentsch, 1967) and the neurotoxin pardaxin (Shai et al., 1988) that lyse both mammalian cells and bacteria.

Antibacterial peptides were initially discovered in invertebrates, and subsequently in vertebrates, including humans. As a complementary or additional defense system, this secondary, chemical immune system provides organisms with a repertoire of small peptides that are synthesized promptly upon induction, and which act against invasion by occasional and obligate pathogens as well as against the uncontrolled proliferation of commensal microorganisms (Boman, 1995). So far, more than 100 different antibacterial peptides have been isolated and characterized. The largest family, and probably the most studied, includes those peptides that are positively charged and adopt an amphipathic α-helical structure. Numerous studies conducted on various native antibacterial peptides tend to emphasize the importance of an amphipathic α-helical structure and a net positive charge for cytolytic activity. The positive charge facilitates interaction of the peptides with the negatively-charged membranes (Andreu et al., 1985) found in higher concentrations in the pathogenic cell membrane as compared to normal eukaryotic cells, and the amphipathic α-helical structure is essential for lytic activity (Chen et al., 1988). Such interactions have been proposed to destroy the energy metabolism of the target organism by increasing the permeability of energy-transducing membranes (Okada and Natori, 1984). Because of their amphipathic structure, it has been suggested that these antibacterial peptides permeate the membrane by forming ion channels/pores via a "barrel-stave" mechanism (Rizzo et al., 1987). According to this model transmembrane amphiphilic α-helices form bundles in which outwardly-directed hydrophobic surfaces interact with the lipid constituents of the membrane, while inwardly facing hydrophilic surfaces produce a pore. Alternatively, the peptides bind parallel to the surface of the membrane, cover the surface of the membrane in a "carpet"-like manner and dissolve it like a detergent (Shai, 1995).

Despite extensive studies, the exact mode of action of short linear non cell-selective peptides, such as pardaxin and melittin, is not known yet, and it is not clear whether similar structural features are required for their cytbtoxicity towards mammalian cells and bacteria.

Pardaxin, a 33-mer peptide, is an excitatory neurotoxin that has been purified from the Red Sea Moses Sole *Pardachirus marmoratus* (Shai et al., 1988) and from the Peacock Sole of the western Pacific *Pardachirus pavoninus* (Thompson et al., 1986). Pardaxin possesses a variety of biological activities depending upon its concentration (reviewed in Shai, 1994). At concentrations below $10^{-7}$ M, pardaxin induces the release of neurotransmitters in a calcium-dependent manner. At higher concentrations of $10^{-7}$ M to $10^{-5}$ M, the process is calcium-independent, and above $10^{-5}$ M cytolysis is induced. Pardaxin also affects the activities of various physiological preparations in vitro. Its biological roles have been attributed to its interference with the ionic transport of the osmoregulatory system in epithelium and to presynaptic activity by forming ion channels that are voltage dependent and slightly selective to cations. A "barrel-stave" mechanism for insertion of pardaxin into membranes was proposed on the basis of its structure and various biophysical studies (reviewed in Shai, 1994). Pardaxin has a helix-hinge-helix structure: the N-helix includes residues 1–11 and the C-helix includes residues 14–26. The helices are separated by a proline residue situated at position 13. This structural motif is found both in antibacterial peptides that can act specifically on bacteria (e.g., cecropin), and in cytotoxic peptides that can lyse a variety of cells (e.g., melittin).

Melittin, a 26-mer amphipathic peptide, is the major component of the venom of the honey bee *Apis mellifera* (Habermann and Jentsch, 1967) and is one of the most studied membrane-seeking peptides (Dempsey, 1990). Melittin is highly cytotoxic for mammalian cells, but is also a highly potent antibacterial agent (Steiner et al., 1981). Numerous studies have been undertaken to determine the nature of the interaction of melittin with membranes, both with the aim of understanding the molecular mechanism of melittin-induced hemolysis and as a model for studying the general features of structures of membrane proteins and interactions of such proteins with phospholipid membranes. Much of the currently described evidence indicates that different molecular mechanisms may underlie different actions of melittin. Nevertheless, the amphipathic α-helical structure has been shown to be a prerequisite for its various activities (Perez et al., 1994).

The structure of melittin has been investigated using various techniques. The results of X-ray crystallography and NMR in methanolic solutions indicate that the molecule consists of two α-helical segments (residues 1–10 and 13–26) that intersect at an angle of 120°. These segments are connected by a hinge (11–12) to form a bent α-helical rod with the hydrophilic and hydrophobic sides facing opposite directions. Four such monomeric melittin molecules cluster together, through hydrophobic interactions, to form a tetramer (Anderson et al., 1980; Bazzo et al., 1988; Terwilliger and Eisenberg, 1982; Terwilliger and Eisenberg, 1982). Upon initial interaction with membrane surfaces, it has been found that the tetramer dissociates to monomers, which retain α-helical conformation prior to insertion into the membrane (Altenbach and Hubbell, 1988).

Melittin shares some similarities with pardaxin. Both pardaxin and melittin are composed of two helices with a proline hinge between them. Furthermore, they exhibit significant homology in their N-helices, which are mostly hydrophobic (Thompson et al., 1986). However, pardaxin (net charge +1) contains an additional seven amino acids residue at its C-terminal side with a charge of −2, while melittin (net charge +6) terminates with an amide group and contains the positively-charged tetrapeptide sequence Lys-Arg-Lys-Arg. There are several functional differences between pardaxin and melittin. Pardaxin binds similarly to both zwitterionic and negatively charged phospholipids (Rapaport and Shai, 1991), while melittin binds better to negatively charged than to zwitterionic phospholipids (Batenburg et al., 1987; Batenburg et al., 1987). Also, pardaxin binds to phospholipids with positive cooperativity (Rapaport and Shai, 1991) while melittin binds with negative cooperativity (Batenburg et al., 1987; Batenburg et al., 1987). Although both pardaxin and melittin are potent antibacterial peptides against Gram-positive and Gram-negative bacteria, pardaxin is 40–100 fold less hemolytic than melittin towards human erythrocytes (Oren and Shai, 1996).

Analogues of pardaxin with L- to D- substitutions were shown to be capable of lysing human erythrocytes (Pouny and Shai, 1992). It was later shown (see results reported below) that two of the peptides disclosed in Pouny and Shai, 1992, namely, D-$Pro^7$-pardaxin and D-$Leu^{18}Leu^{19}$-pardaxin, while being hemolytic, have a very low antibacterial activity. Analogues of magainin with L- to D- substitutions were also found to lack antibacterial activity (Chen et al., 1988).

GLOSSARY

In the following, use will be made of several coined terms for the purpose of streamlining reading of the text and facilitating better understanding of the invention. It should be noted, however, that for complete understanding of these terms, reference will at times be made to the complete description below. These terms and their meaning herein are the following:

"Heterogeneous peptide" as used herein refers to a peptide comprising both D- and L-amino acid residues.

"Homogeneous peptide" as used herein refers to a peptide comprising either only the natural L-amino acid residues, or only D-amino acid residues.

"Homogeneous L-peptide" and "homogeneous D-peptide" as used herein refers the homogeneous polypeptide consisting entirely of either L- or D-amino acid residues, respectively.

"Heterogeneous L-based peptide" and "heterogeneous D-based peptide" as used herein refers to a heterogeneous peptide comprising primarily L-amino acid residues, e.g., a peptide derived from homogeneous L-peptide in which one or more of the L-amino acid residues has been replaced by counterpart D-enantiomers, and a heterogeneous peptide comprising primarily D-amino acid residues in which one or more of the D-amino acid residues has been replaced by counterpart L-enantiomers, respectively.

"Helical peptide" as used herein refers to a peptide having a continuous α-helix stretch throughout the major portion of its length. The helical portion of a helical peptide consists entirely of either L-amino acid residues or D-amino acid residues.

"Non-helical peptide" as used herein refers to a peptide which has no α-helix structure or has non-continuous α-helix structures dispersed along its length. A non-helical peptide according to the invention may have an α-helix stretch which, in case it is terminal, has a length spanning less than half a width of a cell's membrane, e.g., less than about 10–15 amino acid residues, and if it is a non-terminal α-helix, has a length which is less than the full width of the cell's membrane, e.g., less than about 20–25 amino acid residues. A non-helical peptide may be a homogeneous peptide with α-helix breaker moieties (see below) or may be a heterogeneous peptide.

"α-helix breaker moiety" as used herein refers to a moiety which if inserted into an α-helix structure disrupts its continuity. Such a moiety may for example be the amino acid residue proline or glycine, α-methyl-substituted α-amino acids, non-α-amino acids both cyclic and acyclic such as 6-amino-hexanoic acid, 3-amino-1-cyclohexanoic acid, 4-amino-1-cyclohexanoic acid or may be an L- or D-enantiomer inserted into an α-helix stretch consisting of a stretch of amino acid residues of the opposite enantiomer.

"pathogenic cells" as used herein refers to cells which are non-naturally occurring within the body, including cancer cells and pathogenic organisms such as bacteria, fungi, protozoa, virus and mycoplasma, as well as marmalian cells infected with pathogenic organisms such as parasitic protozoans, e.g Leishmania and Plasmodium.

"Selective cytolytic activity" as used herein refers to activity of an agent in inducing cytolysis of a pathogenic cell, the selectivity being manifested in that the agent induces cytolysis of the pathogenic cells at a much lower concentration to that required for the cytolysis of normal non-pathogenic cells such as red blood cells.

"Non-hemolytic" as used herein refers to agents which cause hemolysis of red blood cells at much higher concentrations than the concentration required to cause cytolysis of other cells, such as pathogenic cells such as microorganism cells, cancer cells, and the like.

"Diastereomers" is used herein as a synonym of "heterogeneous peptide".

SUMMARY OF THE INVENTION

The present invention is based on the surprising finding that certain heterogeneous L-based peptides which have non or only a partial, α-helix configuration have a non-hemolytic selective cytolytic activity. This finding is surprising in view of the prevalent concept that peptide-induced cytolysis in cells depends on the α-helix configuration of the amphipathic peptide.

It has thus been realized in accordance with the invention that an α-helical structure is not essential for a peptide to have a cytolytic activity at least on certain cells, e.g., on microorganisms. The α-helical structure is required for mammalian cell lysis but it is not necessary for antibacterial activity.

The present invention thus provides a peptide having a selective cytolytic activity manifested in that:

(a) it has a cytolytic activity on pathogenic cells, being cells which are non-naturally occurring within the body and include pathogenic organisms and malignant cells; and (b) it is non-hemolytic, namely it has no cytolytic effect on red blood cells or has a cytolytic effect on red blood cells at concentrations which are substantially higher than that in which it manifests said cytolytic activity on pathogenic cells.

In one embodiment, the invention provides a non-hemolytic cytolytic peptide having the following characteristics:

(a) it is derived from a non-selective cytolytic natural peptide being (aa) a peptide comprising both L-amino acid residues and D-amino acid residues, or (ab) a peptide comprising one or both of L-amino acid residues and D-amino acid residues, and comprising an α-helix breaker moiety;

(b) the peptide has a net positive charge which is greater than +1; and (c) the peptide is amphipathic.

The non-selective cytolytic natural peptide is for example pardaxin, mellitin or a fragment thereof and the net positive charge may be due to the native amino acid composition, to neutralization of free carboxyl groups, and/or to the addition of positively charged amino acid residues or positively charged chemical groups.

In another embodiment, the invention provides a non-hemolytic cytolytic peptide having the following characteristics:

(a) it is a non-natural synthetic peptide composed of varying ratios of at least one hydrophobic amino acid and at least one positively charged amino acid, and in which sequence at least one of the amnino acid residues is a D-amino acid;

(b) the peptide has a net positive charge which is greater than +1; and (c) the ratio of hydrophobic to positively charged amino acids is such that the peptide is cytolytic to pathogenic cells but does not cause cytolysis of red blood cells.

Examples of positively charged amino acids are lysine, arginine and histidine, and of hydrophobic amino acids are leucine, isoleucine, glycine, alanine, valine, phenylalanine, proline, tyrosine and tryptophan. The net positive charge is due to the amino acid composition, but the addition of positively charged chemical groups may also be considered. In addition, polar amino acids such as serine, threonine, methionine, asparagine, glutamine and cysteine. may be added in order to decrease the hydrophobicity and/or the toxicity of the molecule. In one preferred embodiment, the peptide is composed of one hydrophobic amino acid such as leucine, alanine or valine, and one positively charged amino acid such as lysine or arginine. The synthetic peptide may have at least 6, particularly ten or more amino amino acid residues. In one preferred embodiment, the synthetic diastereomer is a 12-mer peptide composed of leucine, alanine or valine and lysine, and at least one third of the sequence is composed of D-amino acids.

In a further embodiment, the non-hemolytic cytolytic peptide of the invention is a cyclic diastereomer of a peptide derived from a non-selective cytolytic natural peptide or of a non-natural synthetic peptide as described above, or of a fragment thereof. These cyclic diastereomers are obtained by conventional cyclization methods for peptides. In one embodiment, the cyclic diastereomer is derived from the fragment 1–22 of pardaxin to which 1 to 3 Lys residues have been added to the N-terminus and cysteine residues have been added to both N- and C-terminus for cyclization.

In still another embodiment, the invention provides a non-hemolytic cytolytic plurality of 2 or more non-hemolytic cytolytic peptides of the invention complexed or “bundled” together, e.g. by the use of a linker or “template” molecule covalently bound to each of the peptides. The bundle may be composed of 2 or more, preferably 5, molecules of the same peptide or of different peptides. The linker /template may be a peptide of the invention or a commonly used linker, e.g. polymers such as polyesters, polyamides, polypeptides, polyaminoacids (e.g. polylysine) carrying active groups such as OH, SH, COOH, $NH_2$, $CH_2Br$.

In still a further embodiment, the invention provides a non-hemolytic cytolytic mixture of hydrophilic diastereomers of the invention obtained by adding a mixture composed of 1 eq each of the desired hydrophobic, positively charged and D-amino acid at each coupling step of the solid phase method for peptide synthesis. In this way, a mixture of 312 different peptides were obtained with a mixture of lysine, leucine and D-leucine, and the hydrophilic mixture was obtained therefrom after HF cleavage, extraction with water and lyophilization.

In a further embodiment, the invention provides non-hemolytic cytolytic random copolymers consisting of different ratios of a hydrophobic, a positively charged and a D-amino acid, e.g. 1:1:1, 2:1:1 and 3:1:1 (Mol) copolymers of Lys:Leu: D-Leu.

Preferably, the non-hemolytic cytolytic peptide in accordance with the invention has either no α-helix structure or has an α-helix structure which length is insufficient to span the width of a cell membrane. The peptide of the invention thus does not contain an uninterrupted stretch of either all D- or all L-amino acid residues of a length capable of s forming part of a transmembrane pore. Such a length is typically about 20–22 amino acids, where the stretch is in the non-terminal portion of the peptide and about half, i.e., 10–11 amino acids, where the stretch is in the terminus of the peptides, since in such a case two peptides may join their terminus together and span the cell’s membrane.

The disruption of a stretch of D- or L-amino acid residues may be carried out by replacement of one or more amino acids in the stretch by the amino acid of the opposite enantiomer or by placing in the continuous stretch an α-helix breaker moiety such as proline, glycine, an CL-methyl-α-amino acid or a non-α-amino acid.

The peptides of the invention have a net positive charge greater than +1. The net positive charge may be due to the native amino acid composition of the invention, to neutralization of free COOH groups, for example by amidation, or may be due to addition of positively charged amino acids or chemical groups. It was found that the selective cytolytic activity can at times be enhanced by increasing the net positive charge, for example, by attaching at any position in the molecule a positively charged amino acid and/or a positively charged group. For example, a polyamine group, an alkylamino group or amino alkylamino group, etc., may be attached at one of its terminals, typically, at its carboxyl terminal. A preferred such group is the aminoethylamino group $—NH—CH_2—CH_2—HH_2$, designated hereinafter “TA”.

The peptides of the invention that are derived from non-selective cytolytic natural peptides, e.g. pardaxin and melittin, are amphipathic, meaning that they have one surface which is mainly composed of hydrophobic amino acid residues and an opposite surface which is mainly composed of hydrophilic amino acid residues. The amphipathic nature of peptides which fall under the scope of the invention may be verified according to methods known in the art. An example of such a method is the use of a Shiffer and Edmondson wheel projection wherein the amino acid residues are written, according to their sequence in a circle so that each amino acid in the sequence is angularly displaced by 100° from its neighboring amino acid residues (3.6 amino acids per circle). If most hydrophilic amino acids concentrate on one side of the wheel and hydrophobic amino acids concentrate on the opposite side of the wheel then the peptide may be considered amphipathic.

The peptides of the invention that are not derived from non-selective cytolytic natural peptides, e.g. the synthetic diastereomers composed of hydrophobic, positively charged and D-amino acids, are not amphipathic. They have a net positive charge greater than +1 and a suitable hydrophobic to positively charged amino acid ratio such that the resulting peptide is cytolytic to pathogenic cells but not hemolytic. These peptides can be screened very easily according to the invention by using the antibacterial and hemolytic tests described herein. In one embodiment, for a peptide composed of leucine and lysine, an appropriate Leu:Lys ratio may be 64%:36% for a diastereomer of 6 amino acid residues, and 66%:34% for a diastereomer of 12 amino acid residues Without wishing to be bound by theory, it is believed however that the cytolytic activity may be the result of aggregation of a number of peptides on the surface of the membrane and together such peptides cause lesion of the cell membrane. Accordingly, as described above, it is contemplated in accordance with the invention also to use a plurality of peptides of the invention complexed (or bundled) together, e.g., by the use of a linker molecule covalently bound to each of the peptides.

The individual peptide of the invention typically consists of at least six, and preferably ten or more amino acid residues. In a complex of the invention, each individual peptide may typically have a length of above 5 amino acid residues.

By a preferred embodiment, the non-hemolytic cytolytic peptide is a heterogeneous peptide comprising both D- and L-amino acid residues, i.e. a diastereomer, having a selective cytolytic activity on pathogenic cells, the selectivity being manifested in that the peptide induces cytolysis of the pathogenic cell at a much lower concentration to that in which it induces hemolysis, i.e., cytolysis of red blood cells.

The present invention also provides a pharmaceutical composition comprising a non-hemolytic cytolytic peptide of the invention as the active agent, and a pharmaceutically acceptable carrier. The compositions are for use in the treatment of diseases or disorders caused by different pathogenic organisms such as Gram-positive and Gram-negative bacteria, virus, fungi, mycoplasma, and parasitic protozoans, e.g Leishmania that causes leishmaniasis and Plasmodium that causes malaria. In a preferred embodiment, the anti-pathogenic composition is an antimicrobial, particularly antibacterial compositions. In addition, the compositions of the invention are useful against malignant cells and can be used in the treatment of cancer.

Also provided by the present invention is a method of treatment comprising administering said hemolytic non-cytolytic peptide to a subject in need. The method of the invention as well as the above composition are applicable in both human and veterinary medicine.

Further provided in accordance with the invention is also the use of said non-hemolytic cytolytic peptide in the preparation of a pharmaceutical composition for the treatment of a disease or a disorder in human or a non-human animal, in particular antibacterial compositions.

In a further embodiment, the selective peptides of the invention can be used as disinfectants for the destruction of microorganisms, i.e., in solution for wetting contact lenses, may be used as preservatives, for example in the cosmetic or food industry, and as pesticides, e.g. fungicides, bactericides, in agriculture, or for preservation of agricultural products, e.g. fruits and legumes.

BRIEF DESCRIPTION OF THE DRAWINGS

FIG. 14A, control; FIG. 14B, *E. coli* treated with [D]-$L^{3,4,8,10}$-$K_3L_9$; FIG. 14C, E. coli treated with [D]-$L^{3,4,8,10}$-$K_4L_8$ ; FIG. 14D, *E. coli* treated with [D]-$L^{3,4,8,10}$-$K_5L_7$; FIG. 14E, *E. coli* treated with [D]-$L^{3,4,8,10}$-$K_7L_5$; FIG. 14F, control; FIG. 14G, *E. coli* treated with [D]-$L^{3,4,8,10}$-$K_4L_9$; FIG. 14H, *E. coli* treated with [D]-$L^{3,4,8,10}$-$K_5L_7$.

DETAILED DESCRIPTION OF THE INVENTION

Figure 1:
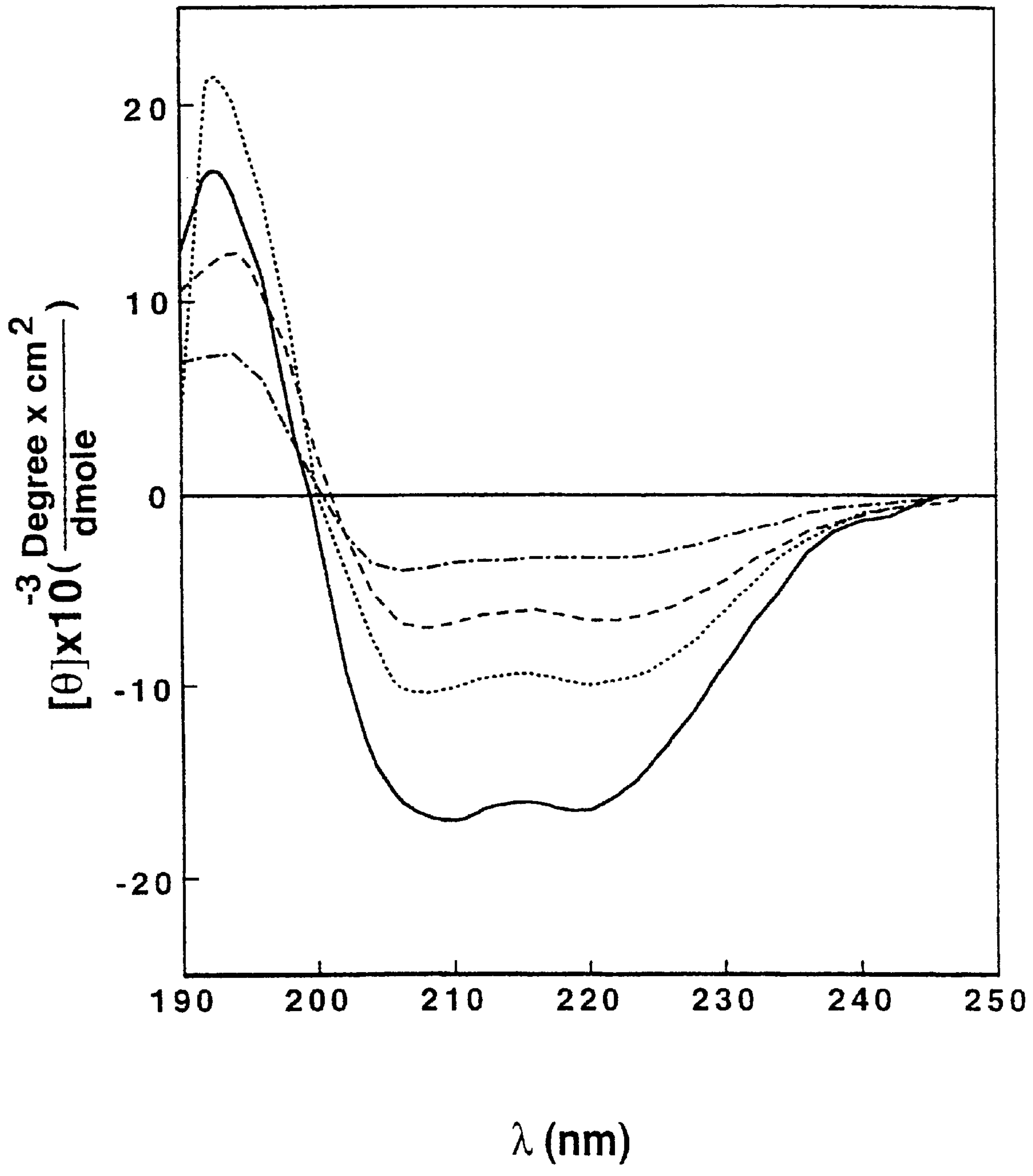
FIG. 1 shows circular dichroism (CD) spectra of aminoethylarninopardaxin (TApar)-derived peptides. Spectra were taken at peptide concentrations of 0.8–2.0×$10^{-5}$ M in 40% 2,2,2-trifluoroethanol (TFE)/water. Symbols: TApar (—); [P]$P^7$-TApar ( . . . ); [D]$L^{18}L^{19}$-TApar (—) and [D]$P^7L^{18}L^{19}$-TApar (·—·—)

It was surprisingly found in accordance with the present invention that heterogeneous L-based peptides possess selective cytolytic activity manifested by a selective destruction of pathogenic cells, e.g., bacteria, with little or no effect on non-pathogenic cells, i.e., red blood cells. This finding is very surprising in view of the prevalent belief in the art that the cytolytic activity of cytolytic peptides in cells, whether pathogenic cells such as bacteria or normal mammalian cells, arises from a single underlying mechanism associated with the α-helix configuration. Without wishing to be bound by theory, these findings of the present invention appear to show that peptide-induced cytolysis is a result of several cytolytic mechanisms, operating in different cells in dependence on the exact nature of the membrane of the target cell; thus by disrupting the α-helix structure of a peptide, for example by replacing some amino acid residues in a homogeneous peptide by the opposite enantiomer, it is possible to obtain a cytolytic peptide which is cytolytically active in one cytolytic mechanism while being inactive in another cytolytic mechanism thus obtaining a cytolytic peptide specific for certain pathogenic target cells.

Herein, fuinctional and structural studies with D-amino acid incorporated analogues (diastereomers) of pardaxin and melittin, two known non-cell selective cytolysins, has been carried in order to understand the molecular mechanism underlying cell selectivity. The data reveal that the resulting diastereomers did not retain their α-helical structure, which caused abrogation of their cytotoxic effects on mammalian cells. However, the diastereomers retained a high antibacterial activity, which was expressed by complete lysis of both Gram-positive and Gram-negative bacteria. Thus, the α-helical structure of pardaxin and meliittin was shown to be important for cytotoxicity against mammalian cells, but not to be a prerequisite for antibacterial activity. However, in another study, a single D-amino acid incorporated into the non-hemolytic antibacterial peptide magainin abolished almost totally its antibacterial activity (Chen et al., 1988). The results herein obtained with pardaxin and melittin diastereomers suggest that hydrophobicity and a net positive charge confer selective antibacterial activity to non-selective cytolytic peptides and that amphipathic α-helical structure is not required. However, the diastereomers of pardaxin and melittin contained long stretches of L-amino acids (14–17 aa long) which raises the possibility that the low residual helicity could be sufficient for membrane binding and destabilization.

To examine whether modulating hydrophobicity and the net positive charge of linear cytotoxic peptides is sufficient to confer selective antibacterial activity, we chose to investigate diastereomers of short model peptides (12 aa. long), composed of varying ratios of leucine and lysine and one third of their sequence composed of D-amino acids. Peptide length and the position of D-amino acids were such that short peptides with very short consecutive stretches of 1–3 L-amino acids that cannot form an α-helical structure were constructed. The diastereomers were evaluated with regard to (1) their cytotoxicity against bacteria and human erythrocytes, (2) their structure, and (3) their ability to interact and perturb the morphology of the bacterial wall and model phospholipid membranes. The data show that modulating hydrophobicity and positive charge is sufficient to confer antibacterial activity and cytolytic selectivity. Furthermore, the resulting antibacterial peptides act synergistically at non lethal concentrations with available antibacterial drugs such as tetracycline, and they are totally resistant to human serum inactivation which dramatically reduces the activity of native antibacterial peptides. Further shorter diastereomers (6 aa and 8 aa long) were prepared and tested and found to be non-hemolytic cytolytic.

The finding that certain cytolytic non-helical peptides have an anti-pathogenic activity, paves the way for the preparation of anti-pathogenic agents, which comprise such non-helical polypeptides. Where the non-helical peptides are heterogeneous peptides composed of both L-amino acids and D-amino acids, the anti-pathogenic agents have the additional advantage of being more resistant to degradation, for example by proteases, than homologous L-peptides, on the one hand, and on the other hand, are not completely degradation-resistant as the full homologous D-peptides. Resistance to degradation may be disadvantageous in view of slow clearance from the body with possible associated toxic side effects. The non-α-helical antipathogenic peptides may be used in a variety of therapeutic procedures.

Since it is known that homologous D-peptides possess essentially identical cytolytic activity to the corresponding homologous L-peptides (Bessalle et al., 1990) then accordingly it is clear that heterogeneous D-based peptides possess the same antipathogenic properties as heterogeneous L-based peptides.

The finding of the present invention, i.e., that certain non-α-helical peptides have a cytolytic activity against bacteria without a cytolytic activity against red blood cells, is a result of the fact that bacterial cells differ from red blood cells in the composition of their cell membrane. Differences in the composition of the cell membrane can also be found among a variety of pathogenic cells, such as cancer cells, and normal cells. Thus, based on the finding of the present invention, that certain non-α-helical peptides possess a specific cytolytic activity against one type of cells, i.e., bacterial cells, paves the way for development of a variety of drugs having a selective cytolytic activity against one class of cells within the body such as bacteria cells, cells of a parasite, fungus cells, protozoa cells, or cancer cells, with little or no activity against non-pathogenic normal body cells.

The non-hemolytic cytolytic peptides of the invention having a selective cytolytic activity against pathogenic cells, while having a much lower, or no cytolytic activity against normal, non-pathogenic cells, may be used for a variety of therapeutic applications with no or little toxic side effects.

One group of peptides in accordance with the invention are non-α-helical heterogeneous peptides derived from homogeneous peptides with an α-helical structure possessing a broad range cytolytic activity. The present invention thus provides in accordance with one embodiment, a heterogeneous peptide comprising both D- and L-amino acid residues having a sequence such that a homogeneous peptide comprising only L- or only D-amino acid residues and having the same amino acid sequence as said heterogeneous peptide, has an α-helix configuration and has a broad spectrum cytolytic activity manifested on a variety of cells; said heterogeneous peptide having a cytolytic activity on only some of the cells on which said homogeneous peptide is cytolytically active. For example, a cytolytic activity of the heterogeneous peptide is manifested only on pathogenic cells while having no cytolytic activity on normal cells such as red blood cells.

Examples of cytolytic peptides in accordance with the invention are such which are derived from natural peptides which have an α-helical structure and possess a cytolytic activity. The non-α-helical peptides of the invention have a sequence essentially corresponding to the entire or partial sequence of the natural peptide in which D-amino acids are incorporated along the N- and C-helices of the molecule and a net positive charge is attained either by addition of a positively charged amino acid residue, e.g., lysine, arginine, histidine, for example at the N-terminus and/or of a positively charged group, e.g. aminoalkylamino group such as aminoethylamino, for example at the C-terminus of the molecule, or by neutralization of free carboxyl groups e.g. by converting them to amide groups. Examples of such natural peptides are melittin and pardaxin, and fragments thereof.

For example, the non-α-helical peptide may be derived from pardaxin which is a 33-mer peptide or from melittin, which is a 26-mer peptide, the non-α-helical peptide may be a 33-mer or a 26-mer peptide comprising a sequence corresponding to the entire sequence of pardaxin or of melittin, respectively, or may be a non-helical peptide having a sequence corresponding to a partial sequence of pardaxin or melittin, e.g., 8–23 mer melittin sequence. In the case of a heterogeneous peptide derived from pardaxin, the heterogeneous peptide in accordance with the invention may comprise a partial sequence corresponding to that of pardaxin, comprising as little as 10 amino acid residues and ranging between 10 and 24 amino acid residues.

Another group of peptides in accordance with the invention are non-helical peptides which have a sequence having no natural homologs and are composed of at least one hydrophobic and at least one positively charged amino acid and in which sequence at least one amino acid residue is a D-amino acid.

Previous studies with model peptides used to elucidate the structure-function study of antibacterial peptides focused on three parameters; helical structure, hydrophobicity and charge (Anzai et al., 1991; Agawa et al., 1991). Each change in one of these parameters simultaneously resulted in changes in the other two, making it difficult to clarify the unique contribution of each parameter to the overall antibacterial activity. According to the present invention, the effect of the helical structure was eliminated which therefore permitted the study of only two parameters, namely, hydrophobicity and net positive charge, by varying the ratio of leucine and lysine. For this purpose, diastereomers of short model peptides (12 aa. long) containing stretches of only 1–3 consecutive L-amino acids which are too short to form an α-helical structure, were chosen for investigation.

CD spectroscopy revealed that these LeulLys diastereomers are indeed totally devoid of α-helical structure (data not shown), unlike the diastereomers of melittin and pardaxin of the invention which retain low α-helical structure. Nevertheless, the Leu/Lys diastereomers exhibit potent antibacterial activity similar to or greater than that of native antibacterial peptides such as dermaseptin S, or the antibiotic drug tetracycline Moreover, the most potent peptides [D]-$L^{3,4,8,10}$-$K_4L_8$ and [D]-$L^{3,4,8,10}$-$K_5L_7$ (peptides 23 and 24, respectively, of Example 3 herein) were devoid of hemolytic activity against the highly cytolytically-susceptible human erythrocytes. It should be noted that [D]-$L^{3,4,8,10}$-$K_3L_9$ (peptides 22) is devoid of α-helical structure but has considerable hemolytic activity which approaches that of the native cytolytic peptide, pardaxin. This could indicate that the balance between hydrophobicity and positive charge compensates for the amphipathic α-helical structure. However, increasing the positive charge drastically reduced the hemolytic activity while antibacterial activity was preserved, demonstrating that the amphipathic α-helical structure is not required for antibacterial activity.

The interaction of the Leu/Lys diastereomers with both negatively-charged and zwitterionic phospholipid membranes was examined in order to elucidate the basis of their selective cytotoxicity against bacteria. Negatively-charged PE/PG vesicles were used to mimic the lipid composition of *E. coli* (Shaw, 1974), and the zwitterionic PC vesicles to mimic the outer leaflet of human erythrocytes (Verkleij et al., 1973). The biological activity of the Leu/Lys peptides on erythrocytes (FIG. 12) and *E. coli* (Table 5) correlates well with their ability to permeate model membranes. The only peptide which permeated PC vesicles was the only peptide with significant hemolytic activity. These results suggest that the phospholipid composition of the bacterial membrane plays a role in permeation by this family of antibacterial peptides. The ability of antibacterial and non-hemolytic peptides to bind and permeate negatively-charged but not zwitterionic phospholipid vesicles is characteristic of native antibacterial peptides (Gazit et al., 1994), and has been attributed to the fact that the bacterial surface contains lipopolysaccharides (LPS, in Gram-negative bacteria), and polysaccharides (teichoic acids, in Gram-positive bacteria), and their inner membranes contain phosphatidyl glycerol (PG), all of which are negatively charged, while normal eukaryotic cells such as erythrocytes, predominantly express the zwitterionic phospholipid PC on their outer leaflet.

The antibacterial peptide magainin is a non-hemolytic peptide, while melittin, pardaxin, and a model peptide with a sequence similar to that of [D]-$L^{3,4,8,10}$-$K_4L_8$, but composed of entirely L-amino acids, are hemolytic, mainly due to their high hydrophobicity. When the α-helical structure of magainin was disrupted by the introduction of three D-amino acids, the resulting diastereomer had no antibacterial activity (Chen et al.,1988), even though its net positive charge is similar to that of native magainin. Thus, an optimal balance that already exists between the α-helical structure, hydrophobicity and net positive charge of native magainin, allows selective antibacterial activity, and any change in one of these properties could cause a loss in magainin's antibacterial activity. Contrastingly, hydrophobicity appears to play a major role in compensating for the loss of α-helical structure in melittin, pardaxin and the Leu/Lys diastereomers of the invention.

The results according to the invention suggest a new strategy for the design of a repertoire of short, simple, and easily manipulated antibacterial peptides. Each of the diastereomeric model Leu/Lys peptides has a unique spectrum of activity (Table 5). The existence of a repertoire of diastereomeric antibacterial peptides will enable one to choose the most efficacious peptide with regard to the target cell. Furthermore, simultaneous administration of multiple forms of diastereomers peptides, acting separately or in concert, also has a selective survival value, and provides a better shielding against a wider range of infectious microbes. All the Leu/Lys diastereomers displayed increased antibacterial activity against Gram-positive in comparison to Gram-negative bacteria. These results are important considering the increasing resistance of Gram-positive bacteria such as Staphylococcus aureus, enterococci, and pneumococci to conventional antibiotics (Russell et al., 1995). In addition, unlike the native antibacterial peptide dermaseptin S, [D]-$L^{3,4,8,10}$-$K_5L_7$ (peptide 24) retained its antibacterial activity in the presence of pooled human serum.

Figure 14:
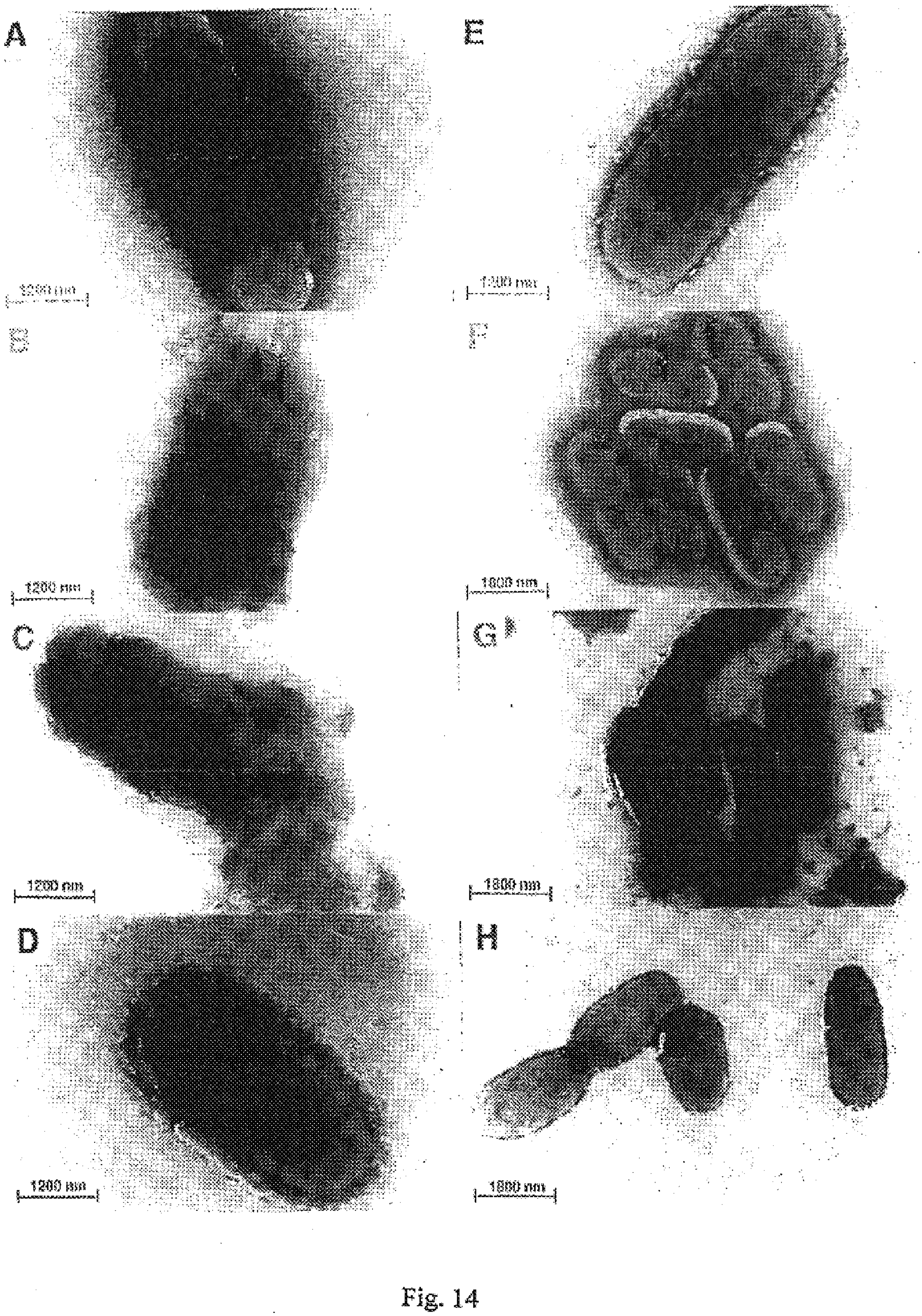
FIGS. 14A–H show electron micrographs of negatively stained *E. coli* untreated and treated with the various Leu/Lys diastereomers at 80% of their MIC.

Diastereomeric peptides should have several advantages over known antibacterial peptides: (1) The peptides should lack the diverse pathological and pharmacological effects induced by α-helical lytic cytolysins. For example, staphylococcus δ-toxin, the antibacterial peptide alamethicin, cobra direct lytic factor and pardaxin exert several histopathological effects on various cells due to pore formation and activation of the arachidonic acid cascade. However, pardaxin diastereomers do not exert these activities. In addition, many amphipathic α-helical peptides bind to calmodulin and elicit several cell responses, and even all D-amino acid α-helices, including melittin have similar activity (Fisher et al.. 1994). Diastereomers with disrupted α-helical structure are not expected to bind to calmodulin; (2) Local D-amino acid substitution would result in controlled clearance of the antibacterial peptides by proteolytic enzymes, as opposed to the total protection acquired by complete D-amino acids substitution (Wade et al., 1990). Total resistance of a lytic peptide to degradation is disadvantageous for therapeutic use. Furthermore, the antigenicity of short fragments containing D,L amino acids is dramatically altered as compared to their wholly L or D-amino acid parent molecules (Benkirane et al., 1993); (3) Total inhibition of bacterial growth induced by the diastereomers, is associated with total lysis of the bacterial wall, as shown by electron microscopy (FIG. 14). Therefore, bacteria might not easily develop resistance to drugs that trigger such a destructive mechanism; (4) [D]-$L^{3,4,8,10}$-$K_5L_7$ (peptide 24) has the ability to perturb the cell wall of bacteria at concentrations lower than their MIC, as seen by electron microscopy (FIG. 14). The simultaneous administration of clinically used antibiotics, which have no activity due to their inability to penetrate the bacterial cell wall, together with peptide 24, may present a solution to this resistance mechanism of bacteria.

It can be summarized that the results obtained herein with pardaxin, melittin and the model peptide diastereomers indicate that neither a specific sequence, length, or position of D-amino acids are required for a polypeptide to have antibacterial activity. However, these factors seem to be more crucial for cytotoxicity towards mammalian cells. These results indicate that only modulating the hydrophobicity and net positive charge of linear cytotoxic polypeptides is sufficient in the design of a repertoire of potent antibacterial diastereomeric polypeptides for the treatment of infectious diseases.

The invention will now be described with reference to some non-limiting drawings and examples.

EXPERIMENTAL PROCEDURES (i) Materials. Butyloxycarbonyl-(amino acid)-(phenylacetamido) methyl resin was purchased from Applied Biosystems (Foster City, Calif.) and butyloxycarbonyl (Boc) amino acids were obtained from Peninsula Laboratories (Belmont, Calif.). Other reagents used for peptide synthesis included trifluoroacetic acid (TFA, Sigma), N,N-diisopropylethylamine (DIEA, Aldrich. distilled over ninhydrin), dicyclohexylcarbodiimide (DCC, Fluka), 1-hydroxybenzotriazole (HOBT, Pierce) and dimethylformamide (peptide synthesis grade, Biolab). Egg phosphatidylcholine (PC) and phosphatidylserine (PS) from bovine spinal cord (sodium salt-grade I) were purchased from Lipid Products (South Nutfield, U.K). Egg phosphatidylglycerol (PG) and phosphatidylethanolamine (PE) (Type V, from *Escherichia coli*) were purchased from Sigma. Cholesterol (extra pure) was supplied by Merck (Darmstadt, Germany) and recrystallized twice from ethanol. 3,3'-Diethylthio-dicarbocyanine iodide [diS-$C_2$-5] was obtained from Molecular Probes (Eugene, Oreg.). Native melittin was purchased from Sigma. Commercially available melittin usually contains traces of phospholipase $A_2$, which causes rapid hydrolysis of phospholipids. Therefore, special care was taken to remove all the phospholipase $A_2$ from melittin using RP-HPLC. All other reagents were of analytical grade. Buffers were prepared in double glass-distilled water.

(ii) Peptide synthesis and purifcation. Peptides were synthesized by a solid phase method on butyloxycarbonyl-(amino acid)-(phenylacetamido) methyl resin (0.05 meq) (Merrifield et al., 1982). The resin-bound peptides were cleaved from the resins by hydrogen fluoride (HF), and after HF evaporation extracted with dry ether. These crude peptide preparations contained one major peak, as revealed by RP-HPLC, that was 50–70% pure peptide by weight. The synthesized peptides were further purified by RP-HPLC on a $C_{18}$ reverse phase Bio-Rad semi-preparative column (300 Å pore size). The column was eluted in 40 min, using a linear gradient of 10–60% acetonitrile in water, both containing 0.05% TFA (v/v), at a flow rate of 1.8 ml/min. The purified peptides, which were shown to be homogeneous (~95%) by analytical HPLC, were subjected to amino-acid analysis and to mass spectrometry to confirm their sequences.

(iii) Transamination of the peptides. The resin-bound peptides as in (ii) above were transaminated with 30% ethylene diamine in DMF for 3 days, followed by filtration of the resin, precipitation of the protected peptides, namely aminoethylamino (TA) peptides, with ether and removal of the protecting groups with HF. The synthetic TA-peptides were purified (>95% homogenicity) by reverse-phase HPLC on a $C_{18}$ column using a linear gradient of 25–80% acetonitrile in 0.1% TFA, in 40 min, and then subjected to amino acid analysis to confirm their composition.

(iv) Amidation of thepeptides. Resin-bound peptide (20 mg) was treated for 3 days with a mixture composed of 1:1 v/v of saturated ammonia solution (30%) in methanol and DMSO (1:1 v/v) which resulted in amidation of the carboxylate group of the glutamine residue located at the C-terminus of [D]-$V^{5,8}$,$I^{7}$,$K^{21}$-melittin. Thus, peptides were obtained in which all the protecting groups remained attached, but whose C-terminal residues were modified by one amide group. The methanol and ammonia were evaporated under a stream of nitrogen, and the protected peptides were extracted from the resin with DMSO, and precipitated with dry ether. The products were then subjected to HF cleavage and to further purification using RP-HPLC as described above.

(v) Preparation of lipid vesicles. Small unilamellar vesicles (SUV) were prepared by sonication of PC/cholesterol (10:1 w/w) or PC/PS (1:1 w/w) dispersions. Briefly, dry lipid and cholesterol (10:1 wlw) were dissolved in a $CHCl_3$/MeOH mixture (2:1 v/v). The solvents were then evaporated under a stream of nitrogen and the lipids (at a concentration of 7.2 mg/ml) were subjected to a vacuum for 1 h and then resuspended in the appropriate buffer, by vortexing. The resultant lipid dispersions were then sonicated for 5–15 min in a bath type sonicator (G1125SP1 sonicator, Laboratory Supplies Company Inc., NY) until clear. The lipid concentrations of the resulting preparations were determined by phosphorus analysis Bartlett, 1959). Vesicles were visualized using a JEOL JEM 100B electron microscope (Japan Electron Optics Laboratory Co., Tokyo, Japan) as follows. A drop of vesicles was deposited on a carbon-coated grid and negatively stained with uranyl acetate. Examination of the grids demonstrated that the vesicles were unilamellar with an average diameter of 20–50 nm (Papahadjopoulos and Miller, 1967).

(vi) Preparation of serunl Blood was collected from five volunteers and allowed to clot at room temperature for 4 h. The blood was then centrifuged for 15 min at 1500 g, and the serum was removed and pooled. The serum complement was inactivated by heating at 56° C. for 30 min.

(vii) CD Spectroscopy. The CD spectra of the peptides were measured with a Jasco J-500A spectropolarimeter after calibrating the instrument with (+)-10-camphorsulfonic acid. The spectra were scanned at 23° C. in a capped, quartz optical cell with a 0.5 mm path length. Spectra were obtained at wavelengths of 250 to 190 nm. Eight scans were taken for each peptide at a scan rate of 20 nm/min. The peptides were scanned at concentrations of $1.5\times10^{-5}$–$2.0\times10^{-5}$ M in 40% trifluoroethanol (TFE), a solvent that strongly promotes α-helical structure. Fractional helicities (Greenfield and Fasman, 1969; Wu et al., 1981) were calculated as follows:

$$f_h = \frac{[\theta]_{222} - [\theta]^{0}_{222}}{[\theta]^{100}_{222} - [\theta]^{0}_{222}}$$

where $[\theta]_{222}$ is the experimentally-observed mean residue ellipticity at 222 nm, and the values for $[\theta]^{0}_{222}$ and $[\theta]^{100}_{222}$, which correspond to 0% and 100% helix content at 222 nm, are estimated to be 2000 and 32000 deg.$cm^2$/dmole, respectively (Wu et al., 1981).

(viii) Antibacterial activity of the peptides. The antibacterial activity of the diastereomers was examined in sterile 96-well plates (Nunc F96 microtiter plates) in a final volume of 100 μL as follows: Aliquots (50 μl) of a suspension containing bacteria at a concentration of $10^6$ Colony-Forming Units (CFU)/ml LB (Lauria broth) medium were added to 50 μL of water or 66% pooled normal human serum in PBS, containing the peptide in 2-fold serial dilutions. Growth inhibition was determined by measuring the absorbance at 492 nm with a Microplate autoreader El309 (Bio-tek Instruments), following incubation for 18–20 h at 37° C. Antibacterial activity is expressed as the minimal inhibitory concentration (MIC), the concentration at which 100% inhibition of growth was observed after 18–20 h of incubation. The bacteria used were: *Escherichia coli* D21, *Pseudomonas aeruginosa* ATCC 27853, *Acinetobacter calcoaceticus* Acl1, *Salmonella typhimurium* LT2, *Bacillus megaterium* Bml1, *Micrococcus luteus* ATCC 9341, *Bacillus subtilis* ATCC 6051.

(ix) Hemolysis of human red blood cells. The peptides were tested for their hemolytic activities against human red blood cells (hRBC). Fresh hRBC with EDTA were rinsed 3 times with PBS (35 mM phosphate buffer/0.15 M NaCl, pH 7.3) by centrifugation for 10 min at 800 g and resuspended in PBS. Peptides dissolved in PBS were then added to 50 μL of a solution of the stock hRBC in PBS to reach a final volume of 100 μL (final erythrocyte concentration, 5% v/v). The resulting suspension was incubated under agitation for 30 min at 37° C. The samples were then centrifuged at 800 g for 10 min. Release of hemoglobin was monitored by measuring the absorbance of the supernatant at 540 nm. Controls for zero hemolysis (blank) and 100% hemolysis consisted of hRBC suspended in PBS and Triton 1%, respectively.

(x) Visualization of the effects of the peptides on bacteria by electron microscopy. Samples containing *E. coli* ($10^6$ CFU/ml) in LB medium were incubated with the various peptides at their MIC, and one dilution less than the MIC, for 16 h, and then centrifuged for 10 min at 3000 g. The pellets were resuspended and a drop containing the bacteria was deposited onto a carbon-coated grid which was then negatively-stained with 2% phosphotungstic acid (PTA), pH 6.8. The grids were examined using a JEOL JEM 100B electron microscope.

(xi) Membrane permeation induced by the peptides. Membrane permeation was assessed utilizing the diffusion potential assay (Loew et al., 1983; Sims et al., 1974) as previously described (Shai et al., 1991). In a typical experiment, in a glass tube, 4 μl of a liposomes suspension (final phospholipids concentration of 33 μM), in a $K^+$ containing buffer (50 mM $K_2SO_4$, 25 mM HEPES-$SO_4^{-2}$, pH 6.8), was diluted in 1 ml of an isotonic $K^+$ free buffer (50 mM $Na_2SO_4$, 25 mM HEPES-$SO_4^{-2}$, pH 6.8), and the fluorescent, potential-sensitive dye diS-$C_2$-5 was then added. Valinomycin (1 μl of $10^{-7}$ M) was added to the suspension in order to slowly create a negative diffusion potential inside the vesicles, which led to a quenching of the dye's fluorescence. Once the fluorescence had stabilized, which took 3–10 minutes, peptides were added. The subsequent dissipation of the diffusion potential, as reflected by an increase in fluorescence, was monitored on a Perkin Elmer LS-50B spectrofluorometer, with the excitation set at 620 nm, the emission at 670 nm, and the gain adjusted to 100%. The percentage of fluorescence recovery, $F_t$, was defined as:

$$F_t=(I_t-I_0/I_f-I_0)\times100$$

where $I_0$=the initial fluorescence, $I_f$=the total fluorescence observed before the addition of valinomycin, and $I_t$=the fluorescence observed after adding the peptide at time t.

(xii) Binding of peptides to vesicles. The interaction of [D]-$V^{5,8}$,$I^{17}$,$K^{21}$-melittin with vesicles consisting of zwitterionic (PC) or negatively charged phospholipids (PC/PS) was characterized by measuring changes in the emission intensity of the peptides' intrinsic tryptophan in SUV titration experiments. Briefly, SUV were added to a fixed amount of peptide (0.5 $\mu$M) dissolved in buffer containing 50 mM $Na_2SO_4$, 25 mM HEPES-$SO_4^{-2}$, pH 6.8, at 24° C. A 1-cm pathlength quartz cuvette that contained a final reaction volume of 2 ml was used in all experiments. The fluorescence intensity was measured as a function of the lipid/peptide molar ratio (4 separate experiments) on a Perkin-Elmer LS-5 Spectrofluorometer, with excitation set at 280 nm, using a 5 nm slit, and emission set at 340 nm, using a 2.5 nm slit. The binding isotherms were analyzed as a partition equilibrium, using the following formula:

$$X_b = K_P C_f$$

where $X_b$ is defined as the molar ratio of bound peptide ($C_b$) per total lipid ($C_L$), $K_P$ corresponds to the partition coefficient, and $C_f$ represents the equilibrium concentration of the free peptide in solution. For practical purposes, it was assumed that the peptides io initially were partitioned only over the outer leaflet (60%) of the SUV. Therefore, the partition equation becomes:

$$X_b^* = K_P C_f$$

where $X_b^*$ is defined as the molar ratio of bound peptide per 60% of total lipid and $K_P^*$ is the estimated surface partition constant. The curve resulting from plotting $X_b^*$ vs. free peptide, $C_f$ is referred to as the conventional binding isotherm.

(xiii) Tryptophan quenching experiments. Tryptophan which is sensitive to its environrment has been utilized previously in combination with brominated phospholipids (Br-PC) to evaluate peptide localization in the membrane (Bolen and Holloway, 1990; De Kroon et al., 1990). Br-PC employed as quenchers of tryptophan fluorescence are suitable for probing the membrane insertion of peptides, since they act over a short distance and do not drastically perturb the membrane. Melittin and its diastereomer, each of which contains one tryptophan residue, were added (final concentration of 0.5 $\mu$M) to 2 ml of buffer (50 mM $Na_2SO_4$, 25 rmM HEPES-$SO_4^{-2}$, pH 6.8) containing 20 $\mu$l (50 $\mu$M) of Br-PC/PS (1:1 w/w) SUV, thus establishing a lipid /peptide ratio of 100:1. After a 2 min incubation at room temperature, an emission spectrun of the tryptophan was recorded using a Perkin-Elmer LS-50B Spectrofluorometer, with excitation set at 280 nm (8 nm slit). SUV composed of PC/PS (1:1 w/w) and which contained 25% of either 6,7 Br-PC, or 9,10 Br-PC, or 11,12 Br-PC, were used. Three separate experiments were conducted for each peptide. In control experiments, PC/PS (1:1 w/w) SUV without Br-PC were used.

EXAMPLE 1

Synthesis and Biological Activity of Pardaxin-derived Diastereomers 1.1 Synthesis. To examine the role of the $\alpha$-helical structure of a polycationic cytolysin in its cytotoxicity towards mammalian cells and bacteria, a series of pardaxin-derived peptides were synthesized as described in sections (ii) and (iii) of the Experimental Procedures, and characterized for their structure, hemolytic. activity on hRBCs, antibacterial activity and effect on the morphology of bacteria.

Pardaxin (par) is a 33-mer peptide of the following sequence:

Gly-Phe-Phe-Ala-Leu-Ile-Pro-Lys-Ile-Ile-Ser-Ser-Pro-Leu-Phe-Lys-Thr-Leu-Leu-Ser-Ala-Val-Gly-Ser-Ala-Leu-Ser-Ser-Ser-Gly-Gly-Gln-Glu (SEQ ID NO. 1)

Modification of the pardaxin molecule in order to introduce a positive charge was made by either deleting the acidic C-terminus of pardaxin or converting the acidic C-terminus of pardaxin or of a fragment thereof to a positive one by reaction of both carboxyl groups of the Glu residue at the C-terninus with ethylene diamine (TA), and/or adding positively charged amino acid residues such as Lys to the N-terminus, in pardaxin diastereomers in which the N-helix and/or the C-helix were altered by either replacing the residue Pro at position 7 of TApar or of a pardaxin fragment by D-Pro (herein indicated by [D]$P^7$), or the two Leu residues at positions 18 and 19 of TApar or of a pardaxin fragment by D-Leu (herein [D]$L^{18}L^{19}$), or both (herein [D]$P^7$L18$L^{19}$). The D-amino acids were introduced in the centers of the N- and C-helices.

The following pardaxin-derived diastereomers were found to be non-hemolytic and to exhibit selective cytolytic activity (the bold and underlined residues are D-arnino acids). The peptides will be represented hereinafter by numerals in bold.

1. [D]$P^7L^{18}L^{19}$-TApar of the sequence:
Gly-Phe-Phe-Ala-Leu-Ile-Er -Lys-Ile-Ile-Ser-Ser-Pro-Leu-Phe-Lys-Thr-Leu-Leu-Ser-Ala-Val-Gly-Ser-Ala-Leu-Ser-Ser-Ser-Gly-Gly-Gln-Glu-(NH—$CH_2$—$CH_2$—$NH_2$)$_2$
2. [D]$P^7L^{18}L^{19}$[1–22]-TApar of the sequence:
Gly-Phe-Phe-Ala-Leu-Ile-Pro-Lys-Ile-Ile-Ser-Ser-Pro-Leu-Phe-Lys-Thr-Leu-Leu-Ser-Ala-Val-(NH—$CH_2$—$CH_2$—$NH_2$)$_2$
3. [D]$P^7L^{18}L^{19}$[1–22]-par of the sequence:
Gly-Phe-Phe-Ala-Leu-Ile-Pro-Lys-Ile-Ile-Ser-Ser-Pro-Leu-Phe-Lys-Thr-Leu-Leu-Ser-Ala-Val
4. $K^1$[D]$P^7L^{18}L^{19}$[1–22]-TApar of the sequence:
Lys-Gly-Phe-Phe-Ala-Leu-Ile-Pro-Lys-Ile-Ile-Ser-Ser-Pro-Leu-Phe-Lys-Thr-Leu-Leu-Ser-Ala-Val-(NH—$CH_2$—$CH_2$—$NH_2$)$_2$
5. $K^1K^2$[D]$P^7L^{18}L^{19}$[1–22]-TApar of the sequence:
Lys-Lys-Gly-Phe-Phe-Ala-Leu-lle-Er-Lys-Ile-Ile-Ser-Ser-Pro-Leu-Phe-Lys-Thr-Leu-Leu-Ser-Ala-Val-(NH—$CH_2$—$CH_2$—$NH_2$)$_2$
6. $K^1K^2$[D]$P^7L^{18}L^{19}$[1–22]-par of the sequence:
Lys-Lys-Gly-Phe-Phe-Ala-Leu-Ile-Pro-Lys-Ile-Ile-Ser-Ser-Pro-Leu-Phe-Lys-Thr-Leu-Leu-Ser-Ala-Val
7. [D]$P^7$-[1–11]-TApar of the sequence:
Gly-Phe-Phe-Ala-Leu-Ile-Pro-Lys-Ile-Ile-Ser-NH—$CH_2$—$CH_2$—$NH_2$ The following pardaxin derivatives were synthesized and found to be hemolytic as shown in Table 1 hereinafter:

| | | | |
|---|---|---|---|
| 8. | TApar | 9. | [D]$P^{13}$-TApar |
| 10. | [D]$L^5L^{19}$-TApar | 11. | [D]$P^7L^{19}$-TApar |
| 12. | [D]$P^7$-TApar | 13. | [D]$P^7$-par |
| 14. | [D]$L^{18}L^{19}$-TApar | 15. | [D]$L^{18}L^{19}$-par |
| 16. | [D]$P^7L^{18}L^{19}$-par | 17. | [D]$P^7$[1–22]-TApar |

1.2 Determination of the secondary structure of the peptides. The secondary structures of the peptides 1, 8, 12, 14, were evaluated from their CD spectra in 40% TFE, a solvent that strongly promotes an $\alpha$-helical structure, as described in Experimental Procedures, section (vii), and in PBS (35 mM phosphate buffer/0.15 M NaCl, pH 7.0).

The CD spectra of the pardaxin-derived diastereomers are shown in FIG. 1 wherein [8] (—), [12] ( . . . ), [14] ( - - - ), and [1] (—·————·—). As expected, a dramatic decrease in the α-helix content of the peptides was observed as more D-amino acids were incorporated, as reflected by the minima at 208 and 222 nm in 40% TFE. There was a more than 90% decrease in the α-helix content between 8 (TApar) (50% α-helix) and 1 ([D]$P^7L^{18}L^{19}$-TApar) (4%). The α-helix contents of 12 ([D]$P^7$-TApar) and 14 ([D]$L^{18}$ $L^{19}$-TApar) were 25% and 15%, respectively. It should be noted that proline at position 7 does not introduce a kink in the structure but rather participates in the formation of the N-helix as revealed by NMR spectroscopy (Zagorski et al., 1991). In PBS, pardaxin gave a low value of ~12% α-helix content while all the analogues with D-amino acid residues gave very low signals that could not be attributed to specific structures (data not shown).

1.3 Hemolytic and antibacterial activity. The pardaxin-derived peptides 1–17 were then examined for their hemolytic activity towards the highly susceptible human erythrocytes, and for their potential to inhibit the growth of different species of bacteria, as described in Experimental Procedures, sections (ix) and (xviii), respectively. In addition, the cytotoxic bee venom melittin, the antibacterial peptide dermaseptin S, and the antibiotic tetracycline were used as controls.

Figure 2:
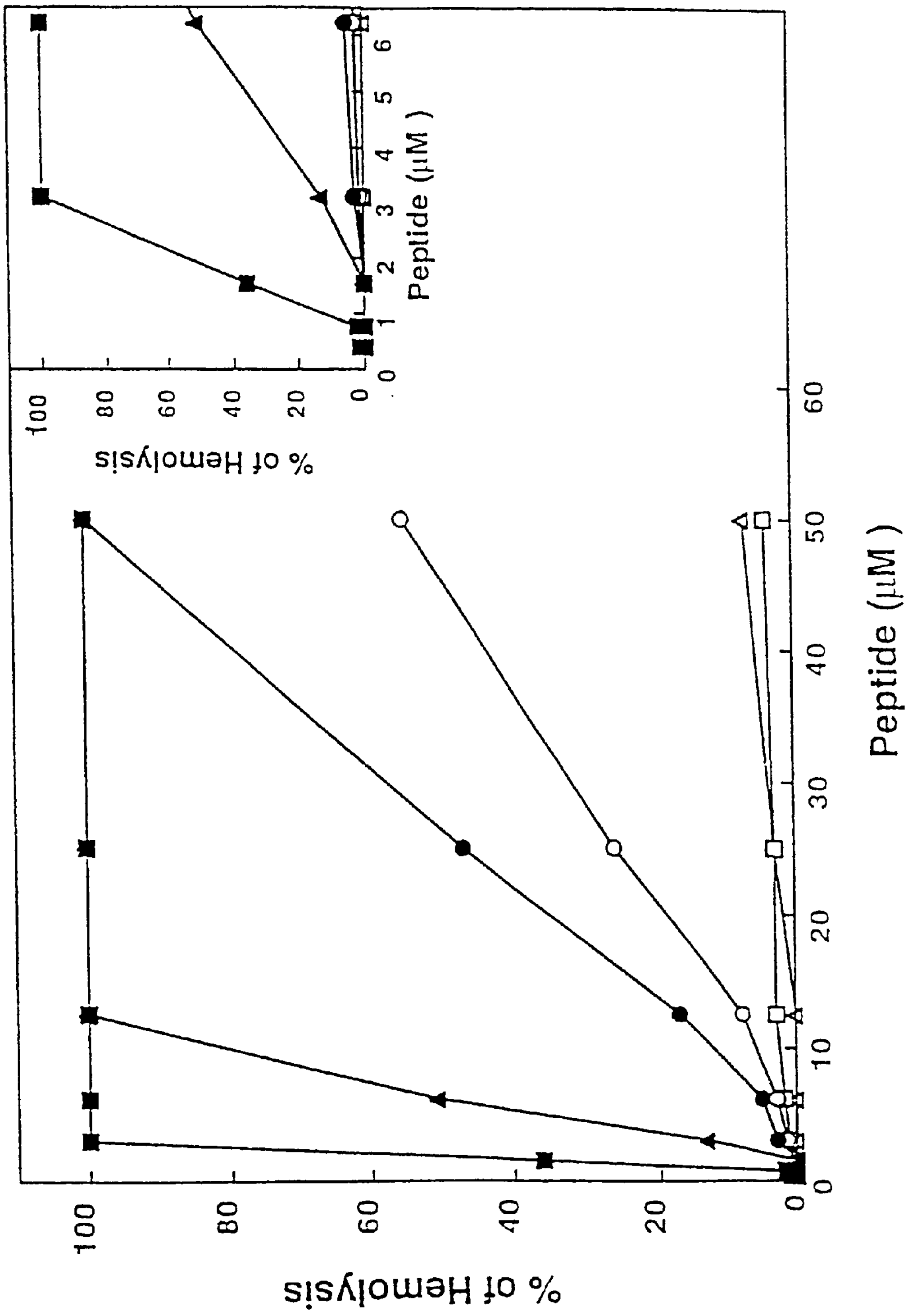
FIG. 2 depicts dose-response curves of the hemolytic activity of TApar-derived peptides towards human red blood cells (hRBC). The inset shows the assay results at low concentration. Symbols: Filled squares, melittin; filled triangles, TApar; filled circles, [D]$P^7$-TApar; empty circles, [D]$L^{18}L^{19}$-TApar; empty squares, [D]$P^7L^{18}L^{19}$-TApar; empty triangles, dermaseptin.

FIG. 2 shows the dose response curves of the hemolytic activity of the peptides 1, 8, 12, 14. It is shown that D-amino acids introduced into TApar dramatically reduced its hemolytic activity, which correlates with the loss of α-helix content in the corresponding analogues. Peptide 8, TApar, with the highest α-helix content is the most hemolytic, while Peptide 1, [D]$P^7L^{18}L^{19}$-TApar, with the lowest α-helix content, is practically devoid of hemolytic activity up to the maximum concentration tested (50 μM). The inability to lyse RBCs is characteristic of most of the naturally occurring antibacterial peptides such as dermaseptin (see FIG. 2), magainin and cecropins.

Table 1 gives the MIC (in μM) of the peptides 1–17 for a representative set of test bacteria, which includes two Gram-negative species, *Escherichia coli* and *Acinetobacter calcoaceticus,* and two Gram-positive species, *Bacillus megaterium* and *Bacillus subtilis,* as well as the % hemolysis at 50 μM peptide. Table 2 gives the MIC (in μM) of the peptides 1, 8, 12, 14 and of melittin, dermaseptin S and tetracycline for some bacterial species The data reveal that despite the dramatic decrease in the α-helix content and hemolytic activity of the diastereomeric analogues 1–7, they all retained most of the potent antibacterial activity of the parent peptide pardaxin, which is comparable to that of known native antibacterial peptides.

TABLE 1

Minimal Inhibitory Concentration (μM) and hemolytic activity of diastereomers pardaxin analogoues.

| | Minimal Inhibitory Concentration (μM) | | | | | | |
|---|---|---|---|---|---|---|---|
| Peptide | *E. coli* (D21) | *A. calcoaceticus* (Ac11) | *B. megaterium* (Bm11) | *M. luteus* (ATCC 9341) | *S. typhimurium* (LT2) | *P. aeruginosa* (ATCC 27853) | % hemolysis at 50 μM peptide |
| 1. | 6 | 6 | 0.9 | 12.5 | N.D | N.D | 5 |
| 2. | 12.5 | 12.5 | 2.5 | N.D[a] | N.D | N.D | 0 |
| 3. | 130 | >130 | 30 | N.D | >130 | >130 | 0 |
| 4. | 7.5 | 7.5 | 1.5 | N.D | N.D | N.D | 0 |
| 5. | 3.5 | 3.5 | 0.75 | N.D | N.D | N.D | 0 |
| 6. | 15 | 6 | 6 | N.D | 120 | 60 | 0 |
| 7. | >120 | >120 | 30 | N.D | >120 | >120 | 0 |
| 8. | 3 | 3 | 0.8 | 5 | 15 | 8 | 100 |
| 9. | 3 | N.D | 1.5 | N.D | N.D | N.D | 83 |
| 10. | 3 | N.D | 1.3 | N.D | N.D | N.D | 56 |
| 11. | 3 | N.D | 1.5 | N.D | N.D | N.D | 82 |
| 12. | 10 | 5 | 1.2 | 5 | N.D | N.D | 49 |
| 13. | 30 | 15 | 3.5 | N.D | >100 | >100 | 23 |
| 14. | 3.5 | 1.5 | 0.6 | 2.5 | N.D | N.D | 100 |
| 15. | 15 | 3.5 | 1.7 | N.D | 60 | 60 | 44 |
| 16. | 100 | 100 | 50 | N.D | >100 | >100 | 0 |
| 17. | 10 | N.D | 1 | N.D | N.D | N.D | 17 |

[a]N.D, not determined.

TABLE 2

| | | Minimum Inhibitory concentration (μM)[a] of the peptides | | | | | | |
|---|---|---|---|---|---|---|---|---|
| Bacterial species | Strain | 8 | 12 | 14 | 1 | Melittin | DermaseptinS | Tetracycline |
| *Escherichia coli* | D21 | 3 | 10 | 3.5 | 6 | 5 | 6 | 1.5 |
| *Acinetobacter calcoacetcus* | Ac11 | 3 | 5 | 2.5 | 6 | 2 | 3 | 1.5 |
| *Bacillus megaterium* | Bm11 | 0.8 | 1.2 | 0.6 | 0.9 | 0.3 | 0.5 | 1.2 |
| *Bacillus subtilis* | ATCC-6051 | 1.5 | 2 | 1.5 | 3 | 0.6 | 4 | 6.5 |

[a]Results are the mean of 3 independent experiments each performed in duplicates, with standard deviation of 20%.

Figure 3:
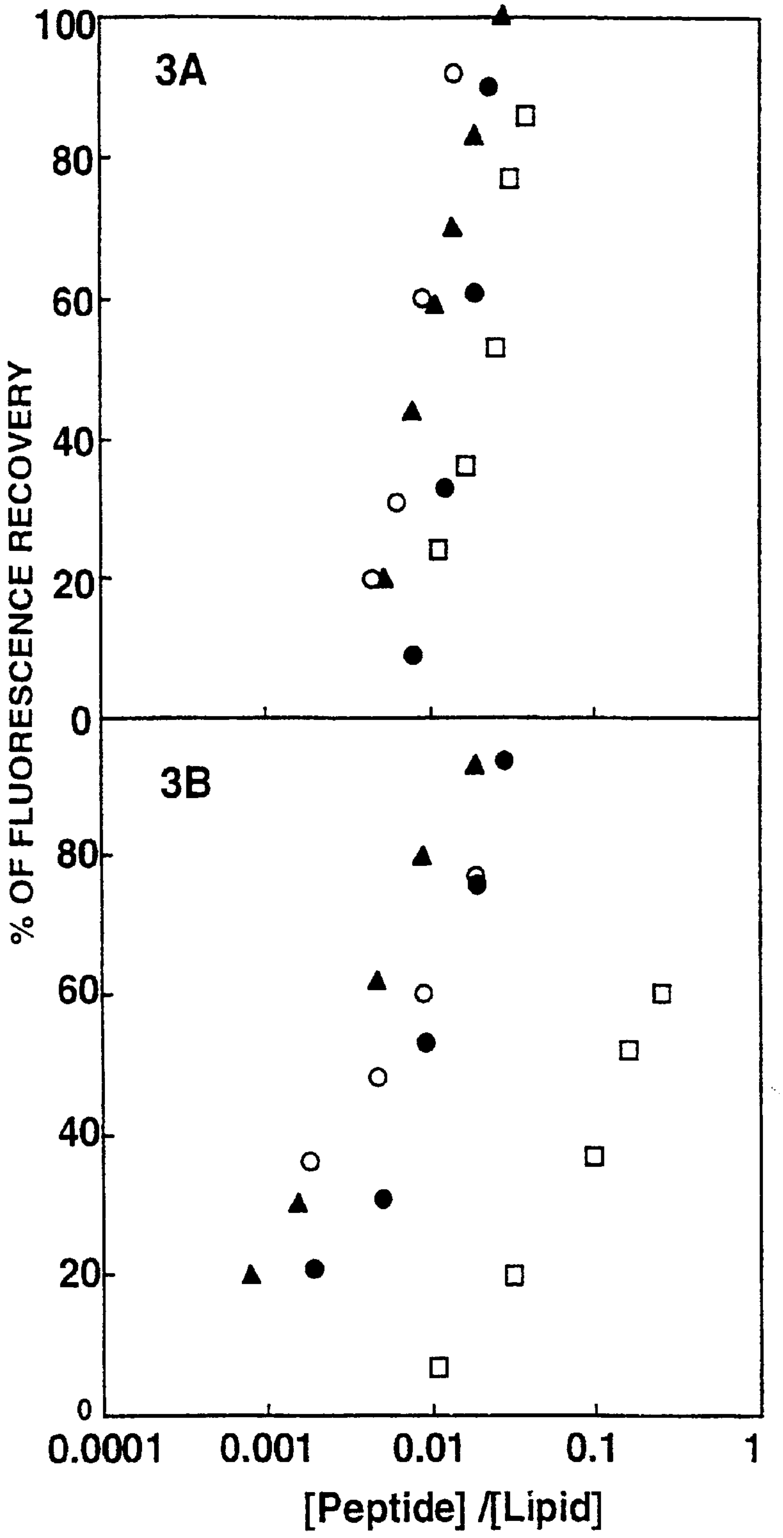
FIGS. 3A–B show the maximal dissipation of the diffusion potential in vesicles induced by the TApar-derived peptides. The peptides were added to isotonic $K^+$ free buffer containing small unilamellar vesicles (SUV) composed of egg phosphatidylcholine/phosphatidylserine (PC/PS) (FIG. 3A) or PC (FIG. 3B), pre-equilibrated with the fluorescent dye diS-$C_2$-5 and valinomycin. Fluorescence recovery was measured 10–20 min after the peptides were mixed with the vesicles. Symbols: Filled triangles, TApar; filled circles, [D]$P^7$-TApar; empty circles, [D]$L^{18}L^{19}$-TApar; empty squares, [D]$P^7L^{18}L^{19}$- TApar.

1.4 Membrane destabilization induced by the pardaxin-derived peptides. A common property of all of the α-helical, positively charged, naturally-occurring antibacterial peptides studied so far, is their ability to interact and permeate negatively charged phospholipids better than zwitterionic phospholipids. The relevance of these findings to their biological target membranes has been attributed to the fact that the surface of bacteria contains lipopolysaccharides (LPS, in Grain-negative bacteria), and polysaccharides (teichoic acids, in Gram-positive bacteria), both of which are acidic, while normal mammalian cells (e.g., erythrocytes) express the predominantly zwitterionic phospholipid PC on their outer leaflet. The dissipation of the diffusion potential to assess the membrane permeating activity of the peptides on both PC and PC/PS phospholipid vesicles (prepared according to Experimental Procedures, section v) was assayed as described in Experimental Procedures, section xi.. The results shown in FIG. 3 for peptides 1, 8, 12, 14, indicate that D-arnino acids introduced into pardaxin did not significantly affect the ability of the peptides to permeate phospholipid membranes. However, peptide 1, the only diastereomer that is devoid of hemolytic activity but retains antibacterial activity, permeates negatively charged phospholipids significantly better than zwitterionic phospholipids. As such it behaves similar to native antibacterial peptides, although it is devoid of α-helical structure. The lack of significant intermediate activities with peptides 12 and 14 might be explained by the fact that they both have either the hydrophobic N-helix or the amphipathic C-helix intact, which is sufficient to promote strong binding to both types of vesicles via hydrophobic interactions.

Figure 4:
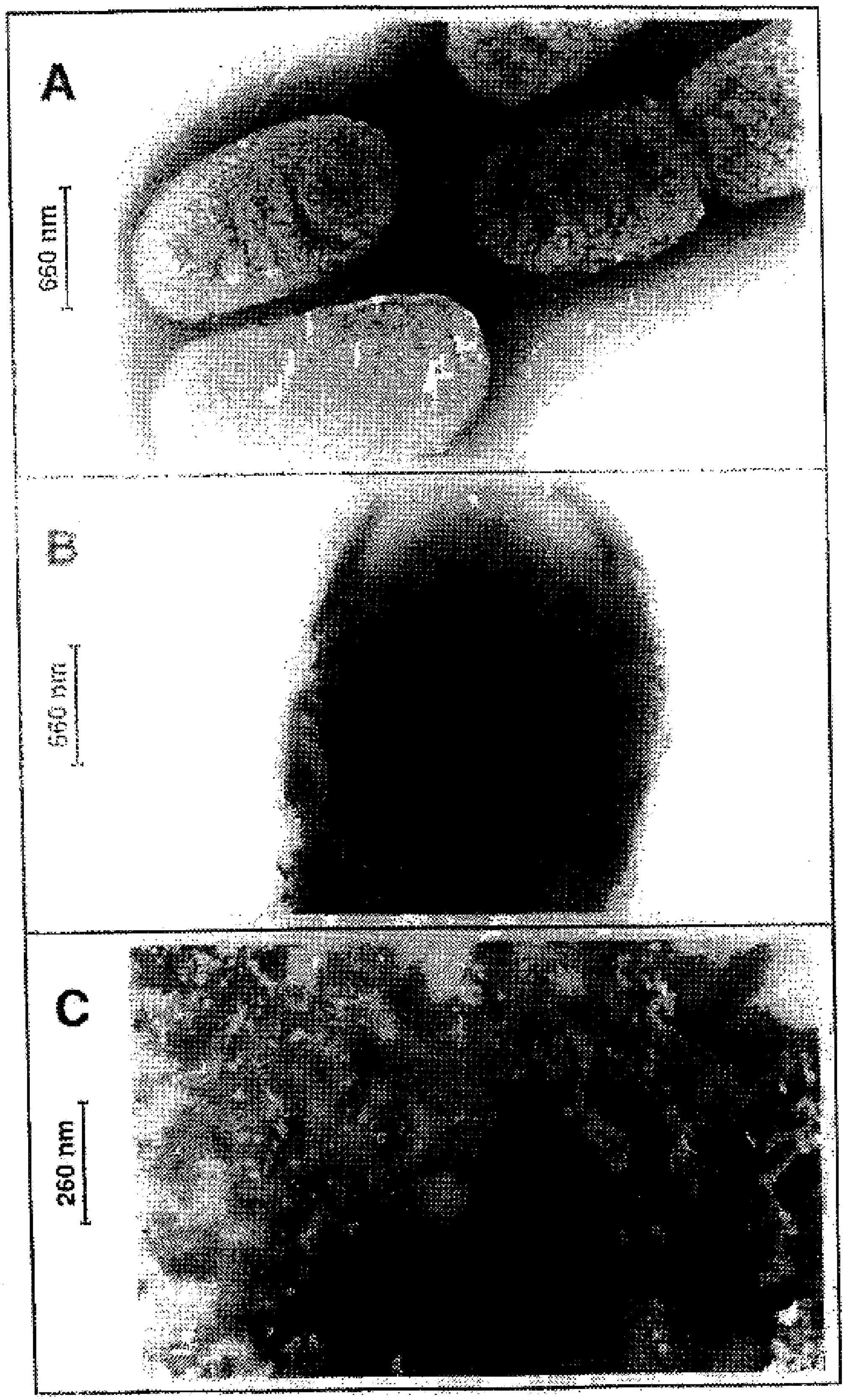
FIGS. 4A–C show electron micrographs of negatively stained *E. coli* cell untreated (FIG. 4A) or treated with [D]$P^7L^{18}L^{19}$-TApar at concentrations lower than the minimal inhibitory concentration (MIC) (4B) or at MIC concentrations (4C)

1.5 Visualization of bacterial lysis using electron microscopy. The effect of the pardaxin-derived peptides on the morphology of intact and treated bacteria was visualized using negative staining electron microscopy, as described in Experimental Procedures, section xx. The peptides were added to bacteria at or below their MIC concentration under the same conditions used in the antibacterial assay (see example 1.3 above). Samples were pulled out after an 18 h incubation and were immediately fixed and examined by transmission electron microscopy. FIG. 4 shows the photographs obtained with the non-hemolytic analogue 1, $[D]P^7L^{18}L^{19}$-TApar, as an example. It was found that at the MIC peptide 1 lysed the bacteria completely, and only small fragments could be observed (FIG. 4C). However, at concentrations lower than the MIC, patches were observed on the bacterial wall (FIG. 4B). These patches might indicate the initial step involved in the lytic process.

EXAMPLE 2

Synthesis and Biological Activity of Melittin-derived Diastereomers 2.1 Synthesis. In order to further examine the role of the α-helical structure of cytolysins in their cytotoxicity against mammalian cells and bacteria and to gain. insight into the mechanism underlying this effect, four diastereomers of melittin (mel) were synthesized.

Melittin is a 26-mer peptide of the sequence:

Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-$NH_2$ (SEQ ID NO: 2)

Modification of the melittin molecule in order to introduce a positive charge was made by converting the acidic C-terminus of melittin or of a fragment thereof to a positive one by reaction of the carboxyl group at the C-terminus with ethylene diamine, in melittin diastereomers in which the N-helix and the C-helix were altered by replacing the two Val residues at positions 5 and 8 of melittin, the Ile residue at position 17 and the Lys residue at position 21 by D-Val, D-Ile and D-Lys, respectively (herein $[D]-V^5V^8I^{17}K^{21}$).

The following melittin-derived diastereomers were found to be non-hemolytic and to exhibit selective cytolytic activity (the bold and underlined residues are D-amino acids):

18. $[D]-V^5V^8I^{17}K^{21}$-mel of the sequence:

Gly-Ile-Gly-Ala-Val-Leu-Lys-Val-Leu-Thr-Thr-Gly-Leu-Pro-Ala-Leu-ILe-Ser-Trp-Ile-Lys-Arg-lys-Arg-Gln-Gln-$NH_2$ 19. $[D]-V^5V^8I^{17}K^{21}$-mel-COOH of the sequence:

Gly-Ile-Gly-Ala-al-Leu-Lys Val-Leu-Thr-Thr-Gly-Leu-Pro-Ala-Leu-Ile-Ser-Trp-Ile-Lys-Arg-Lys-Arg-Gln-Gln-COOH

20. $[D]-V^5V^8I^{17}K^{21}$-[1–22]-TAmel of the sequence:

Gly-Ile-Gly-Ala-Val-Leu-Lys-Val-Leu-Thr-Thr-Gly-Leu-Pro-Ala-Leu-ILe-Ser-Trp-Ile-Lys-Arg-NH—$CH_2$—$CH_2$—$NH_2$

21. $[D]-V^5V^8I^{17}K^{21}$-[4–22]-TAmel of the sequence:

Ala-Val-Leu-Lys-Val-Leu-Thr-Thr-Gly-Leu-Pro-Ala-Leu-Ile-Ser-Trp-Ile-Lys-Arg-NH—$CH_2$—$CH_2$—$NH_2$

The peptides 18–21 were then characterized with regard to their structure, biological function and interaction with bacteria and model membranes composed of either zwitterionic or negatively charged phospholipids.

Figure 5:
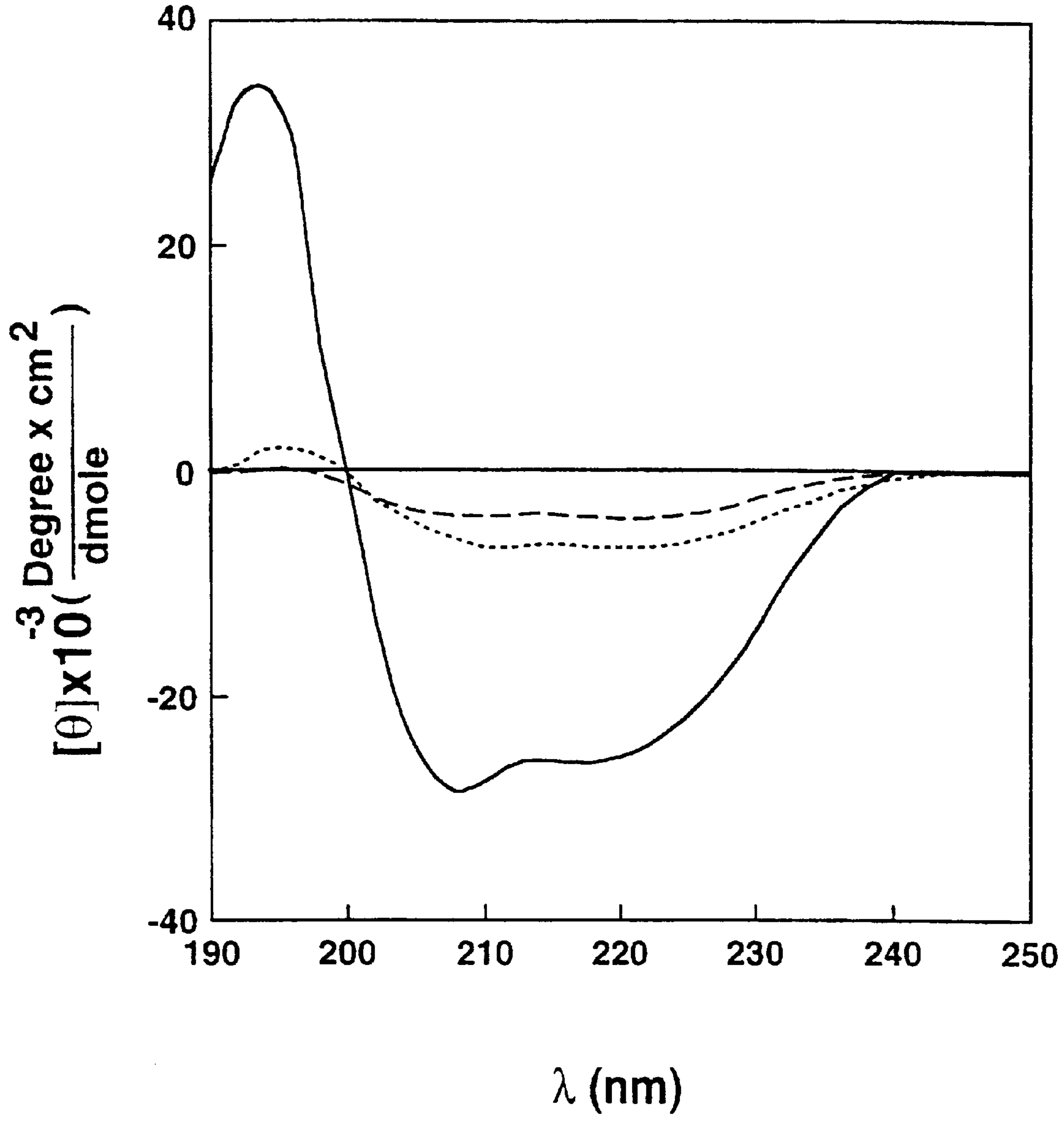
FIG. 5 shows CD spectra of melittin and melittin-derived diastereomers. Spectra were taken at peptide concentrations of 0.8–2.0×$10^{-5}$ M in 40% TFE/water. Symbols: melittin, (——); [D]-$V^{5,8}$,$I^{17}$,$K^{21}$-melittin, ( . . . ); [D]-$V^{5,8}$,$I^{17}$,$K^{21}$-melittin-COOH, ( - - - ).

2.2 CD spectroscopy. The extent of the α-helical structure of the peptides 18 and 19 was determined from their CD spectra in 40% TFE, a solvent that strongly promotes α-helical structure. As expected, the α-helical content of the diastereomers was much lower (80% decrease) than that of melittin, as reflected by the minima at 208 and 222 nm (FIG. 5). The α-helix content of melittin was 73% compared to 15% and 7% in its diastereomers, 18 and 19, respectively.

Figure 6:
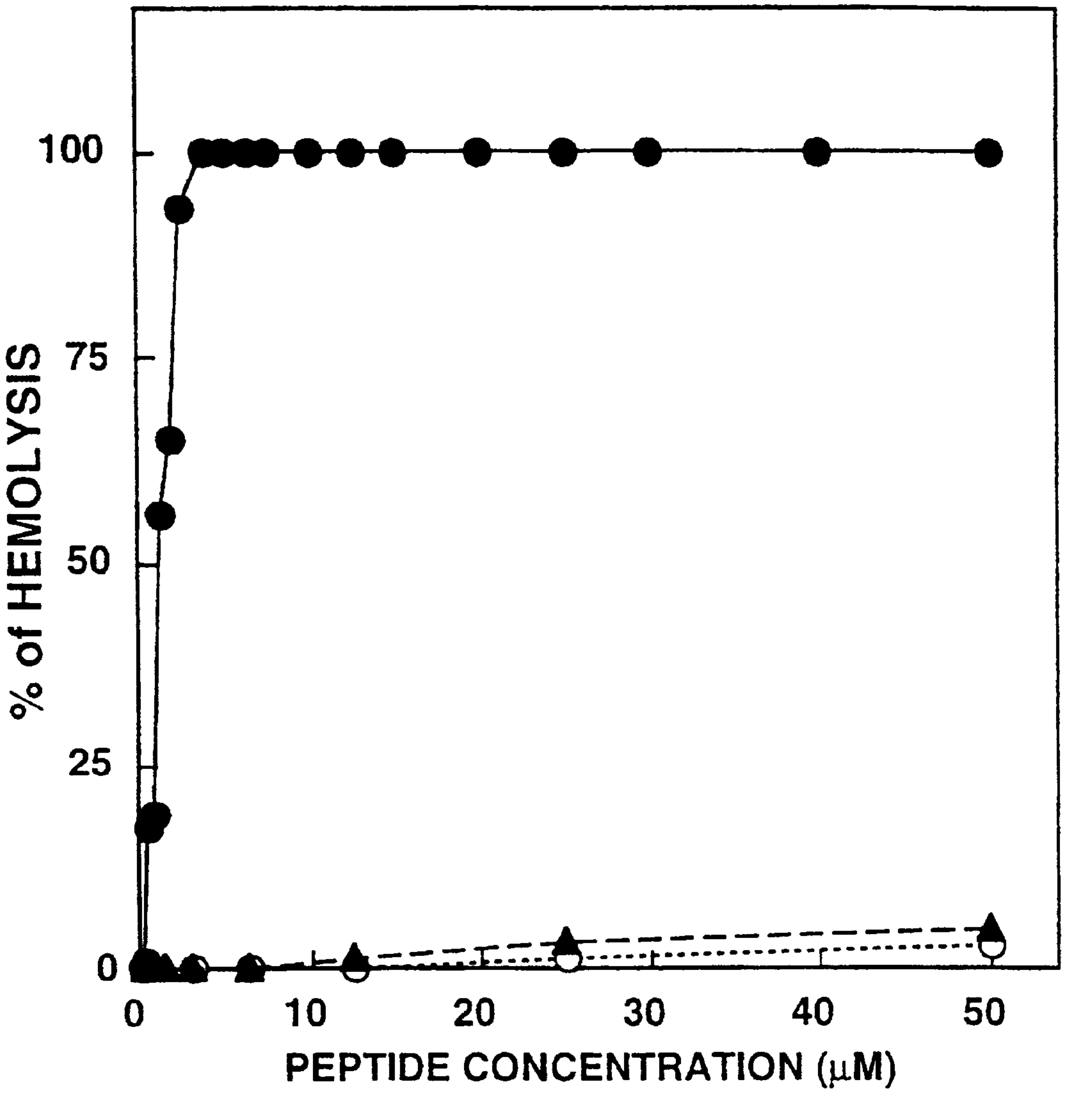
FIG. 6 depicts dose-response curves of the hemolytic activity of the melittin-derived diastereomers towards hRBC. Symbols: filled circles, melittin; empty circles, [D]-$V^{5,8}$,$I^{17}$,$K^{21}$-melittin-COOH; filled triangles, [D]-$V^{5,8}$, $I^{17}$, $K^{21}$-melittin.

2.3 Antibacterial and hemolytic activity of the melittin diastereomers 18–21. The hemolytic activity of the peptides 18–21 against hRBC and their potential to inhibit the growth of different species of bacteria were investigated. The antibiotic tetracycline served as a control in the antibacterial assay. A dose response curve for the hemolytic activity of the peptides was obtained (FIG. 6). Table 3 gives the MIC for a representative set of test bacteria. It can be seen that the introduction of D-amino acids into melittin dramatically reduced its hemolytic activity, which paralleled the loss of the α-helical content in the corresponding analogues. Melittin, with the highest α-helical content was the most hemolytic, while up to the maximum concentration tested (50 $\mu$M), peptides 18 and 19, with the lowest α-helical content, were practically devoid of hemolytic activity. However, despite the dramatic decrease in the hemolytic activity of the melittin diastereomers 18 and 19, they both retained most of the potent antibacterial activity of the parent peptide. Furthermore, the antibacterial activity of peptide 19 was only slightly lower than that of 18, which indicates that the amide group at the C-terminus of melittin does not contribute significantly to the antibacterial activity. In contrast, it is known that cecropin with a free carboxylic C-terrninal has a significant lower antibacterial activity than that of the native cecropin with an amidated C-terminal (Li et al., 1988).

TABLE 3

Minimal Inhibitory concentration (μM) and Hemolytic activity of diastereomer melittin analogues.

| Peptide designation | Minimal Inhibitory Concentration (μM) *E. coli* (D21) | *A. calcoaceticus* (Ac11) | *B. megaterium* (Bm11) | *M. luteus* (ATCC 9341) | *B. subtilis* (ATCC 6051) | % hemolysis at 50 μM peptide |
|---|---|---|---|---|---|---|
| Melittin | 5 | 20 | 0.3 | 0.4 | 0.4 | 100 |
| 18 | 12 | 12 | 0.8 | 25 | 3.5 | 0 |
| 19 | 18 | 18 | 1.2 | 50 | 8 | 0 |
| 20 | 8 | 7 | 0.8 | 29 | N.D | 0 |
| 21 | 21 | 14 | 1.2 | 28 | N.D | 0 |
| Dermaseptin-S | 6 | 3 | 0.5 | N.D | 4 | 9 |
| Tetracycline | 1.5 | 1.5 | 1.2 | N.D | 6.5 | — |

Figure 7:
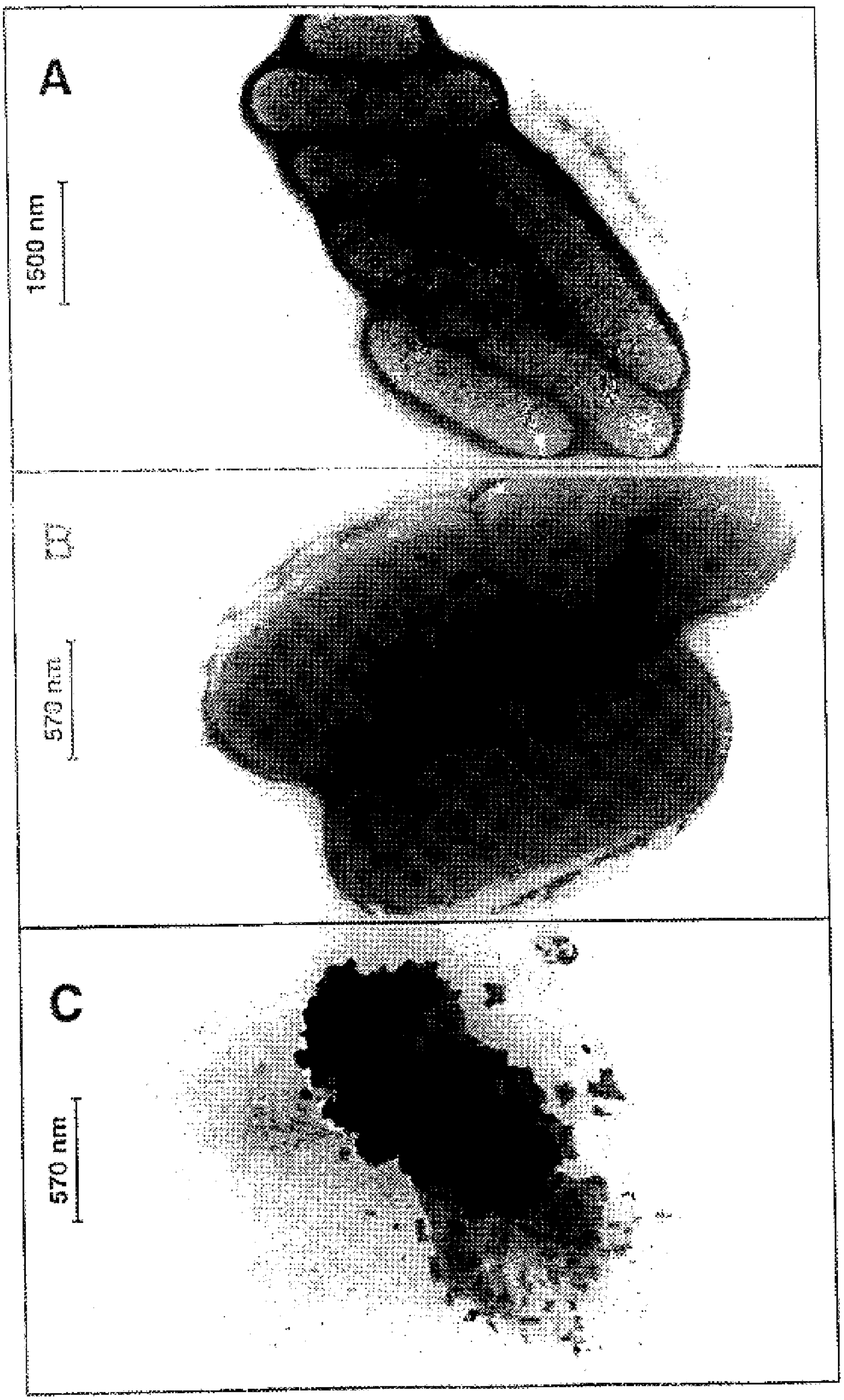
FIGS. 7A–C shows electron micrographs of negatively stained *E. coli* untreated (FIG. 7A) or treated with [D]-$V^{5,8}$, $I^{17}$,$K^{21}$-melittin at concentrations lower than the MIC (7B) or at the MIC concentrations (7C).

2.4 Ellectron microscopy study of bacterial lysis. The effect of the peptide 18 on the morphology of intact and treated bacteria was visualized using transmission electron microscopy. As shown in FIG. 7, at the MIC, the peptide 18 caused total lysis of the bacteria (FIG. 7C). However, at concentrations lower then the MIC, patches were observed on the bacterial wall (FIG. 7B). These patches might represent an initial step in the lytic process.

2.5 Mode of interaction with phospholipid membranes.Since the biological activities of the peptides 18 and 19 were similar, only the mode of interaction of peptide 18 with model phospholipid membranes was compared to that of melittin, in order to elucidate the basis of the membrane selectivity observed. For that purpose the ability of the peptides to dissipate the diffision potential created in both PC and PC/PS vesicles was measured, and the partition coefficients of the peptides with both types of vesicles, and the localization of the peptide when bound to membranes, were determined.

Figure 8:
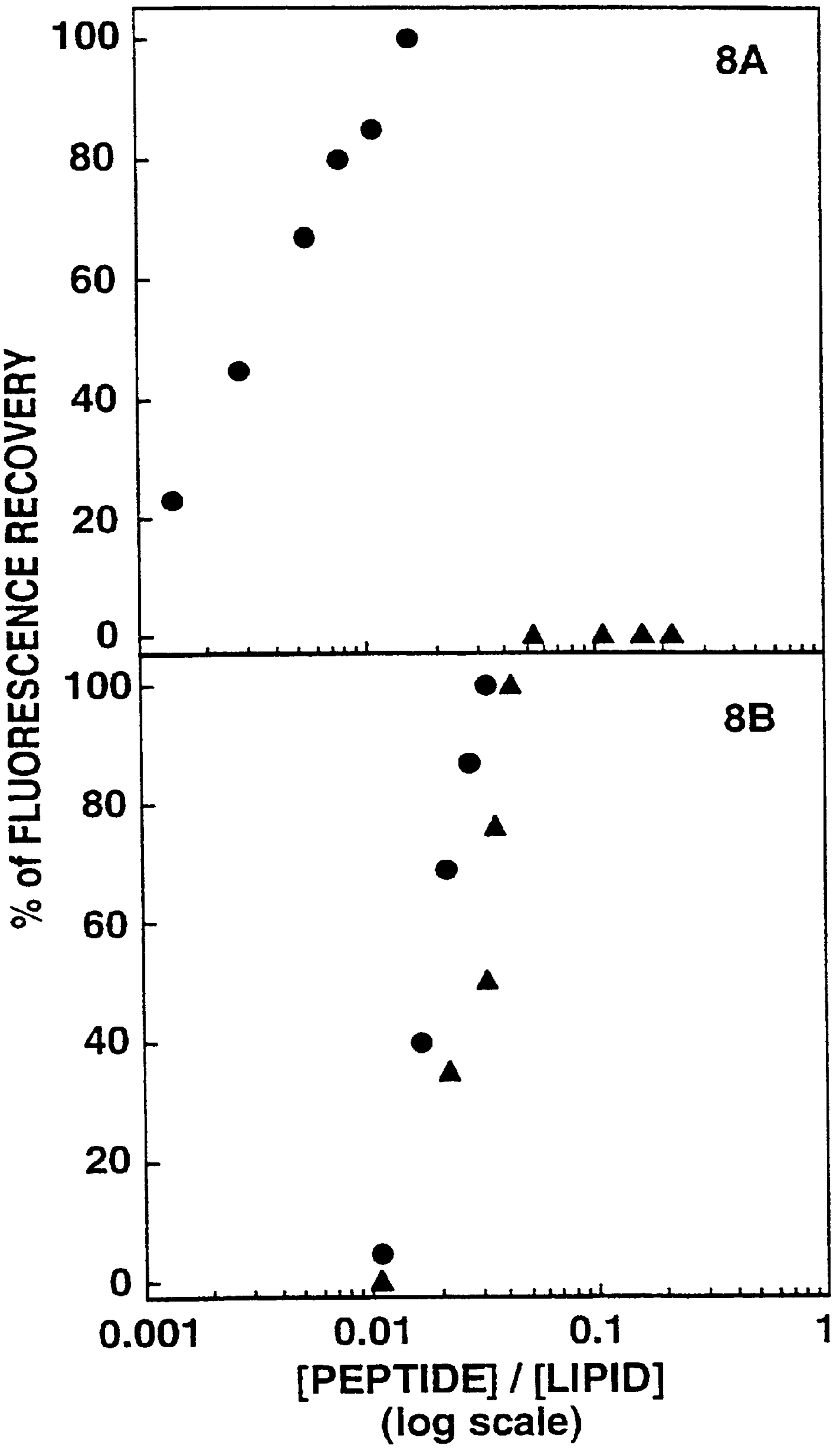
FIGS. 8A–B shows maximal dissipation of the diffusion potential in vesicles induced by melittin and a melittin-derived diastereomer. The peptides were added to isotonic $K^+$ free buffer containing SUV composed of PC (8A) or PC/PS (8B), pre-equilibrated with the fluorescent dye diS-$C_2$-5 and valinomycin. Fluorescence recovery was measured 10–20 min after the peptides were mixed with the vesicles. Symbols: filled circles, melittin; filled triangles, [D]-$V^{5,8}$, $I^{17}$,$K^{21}$-melittin.

2.5.1 Membrane permeability induced by the peptides. Various concentrations of melittin and peptide 18 were mixed with vesicles that had been pre-treated with the fluorescent dye, diS-$C_2$-5, and valinomycin. The kinetics of the fluorescence recovery was monitored with time and the maximum level reached as a function of peptide concentration was determined. As shown in FIG. 8, both melittin and peptide 18 had similar membrane permeating activity with PC/PS vesicles, which demonstrated that introduction of D-amino acids into melittin does not affect the ability of the resulting diastereomer to permeate negatively charged phospholipid (PS/PC) membranes. However, while melittin was also highly active with PC vesicles, the diastereomer was totally devoid of membrane permeating activity with PC vesicles (up to the maximal concentration tested).

Figure 9:
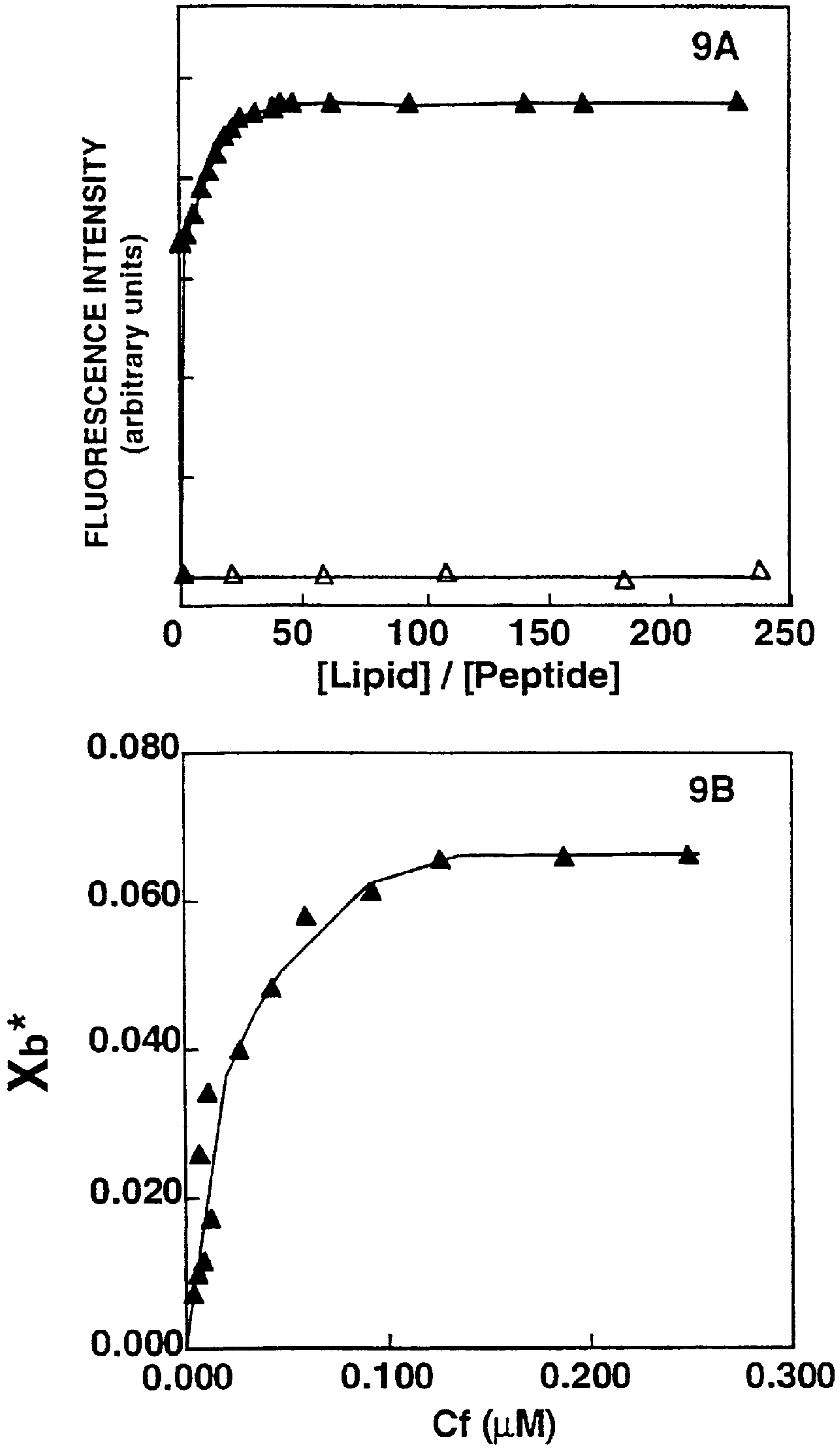
FIGS. 9A–B show increase in the fluorescence of [D]-$V^{5,8}$,$I^{17}$,$K^{21}$-melittin (0.5 gM total concentration) upon titration with PC/PS vesicles (filled triangles) or PC vesicles (empty triangles), with excitation wavelength set at 280 nm and emission at 340 nm. The experiment was performed at 25° C. in 50 mM $Na_2SO_4$, 25 mM HEPES-$SO_4^{-2}$ pH 6.8 (FIG. 9A); and binding isotherm derived from FIG. 9A by plotting $X_b$* (molar ratio of bound peptide per 60% of lipid) versus Cf (equilibrium concentration of free peptide in the solution) (FIG. 9B).

2.5.2 Binding Studies. The inability of the diastereomer 18 to permeate PC vesicles may be due to its inability to bind to PC, or alternatively, it may bind to PC vesicles, but once bound cannot organize into structures that induce membrane leakage. In order to differentiate between these two possibilities, a binding study was conducted. The single Trp residue at position 19 of peptide 18 was used as an intrinsic fluorescence probe to follow its binding to PC and PC/PS vesicles. A fixed concentration (~0.5 μM) of the peptide was titrated with the desired vesicles (PC or PC/PS) and an increase in the fluorescence intensity was observed if binding occurred. Plotting of the resulting increases in the fluorescence intensities of Trp as a function of lipid:peptide molar ratios yielded conventional binding curves (FIG. 9A). The binding curve of peptide 18 with PC/PS reveals that almost all the peptide molecules bound to the vesicles at a lipid:peptide molar ratio of 100:1. However, with PC vesicles a net increase in the fluorescence of the Trp was not observed even with the maximal lipid:peptide molar ratio tested, which indicated that the peptide does not bind to PC vesicles. Binding isotherms were constructed by plotting $X^*_b$ (the molar ratio of bound peptide per 60% of the total lipid) versus $C_f$ (the equilibrium concentration of the free peptide in the solution) (FIGS. 5B). The surface partition coefficients were estimated by extrapolating the initial slopes of the curves to $C_f$ values of zero. The estimated surface partition coefficient, Kp*, of peptide 18 was $1.1\pm0.2\times10^4\ M^{-1}$ (obtained from 4 measurements). This value is similar to the value reported for melittin binding to phosphatidylglycerol/phosphatidylcholine ($4.5\pm0.6\times10^4\ M^{-1}$) (Beschiaschvili and Seelig, 1990).

The shape of the binding isotherm of a peptide can provide information on the organization of the peptide within membranes (Schwarz et al., 1987). The binding isotherm of peptide 18 bend downward indicating a negative cooperativity. A possible explanation for this negative cooperativity is that at low concentration, peptide 18 binding to PS/PC is enhanced by the negative charge of the phospholipid headgroups compared to the partition equilibrium with no charge effect. In addition, upon binding to the membrane the peptide partially neutralizes the negative membrane surface charge. However, once the membrane surface charge is neutralized, further peptide 18 binding is difficult, since repulsion of like charges becomes the dominant factor. Similar results were obtained in studies of melittin binding to negatively charged phospholipid membranes) (Batenburg et al., 1987; Beschiaschvili and Seelig, 1990). Interestingly, unlike melittin which binds strongly also to PC vesicles (Kuchinka and Seelig, 1989), peptide 18 did not bind to PC vesicles.

Figure 10:
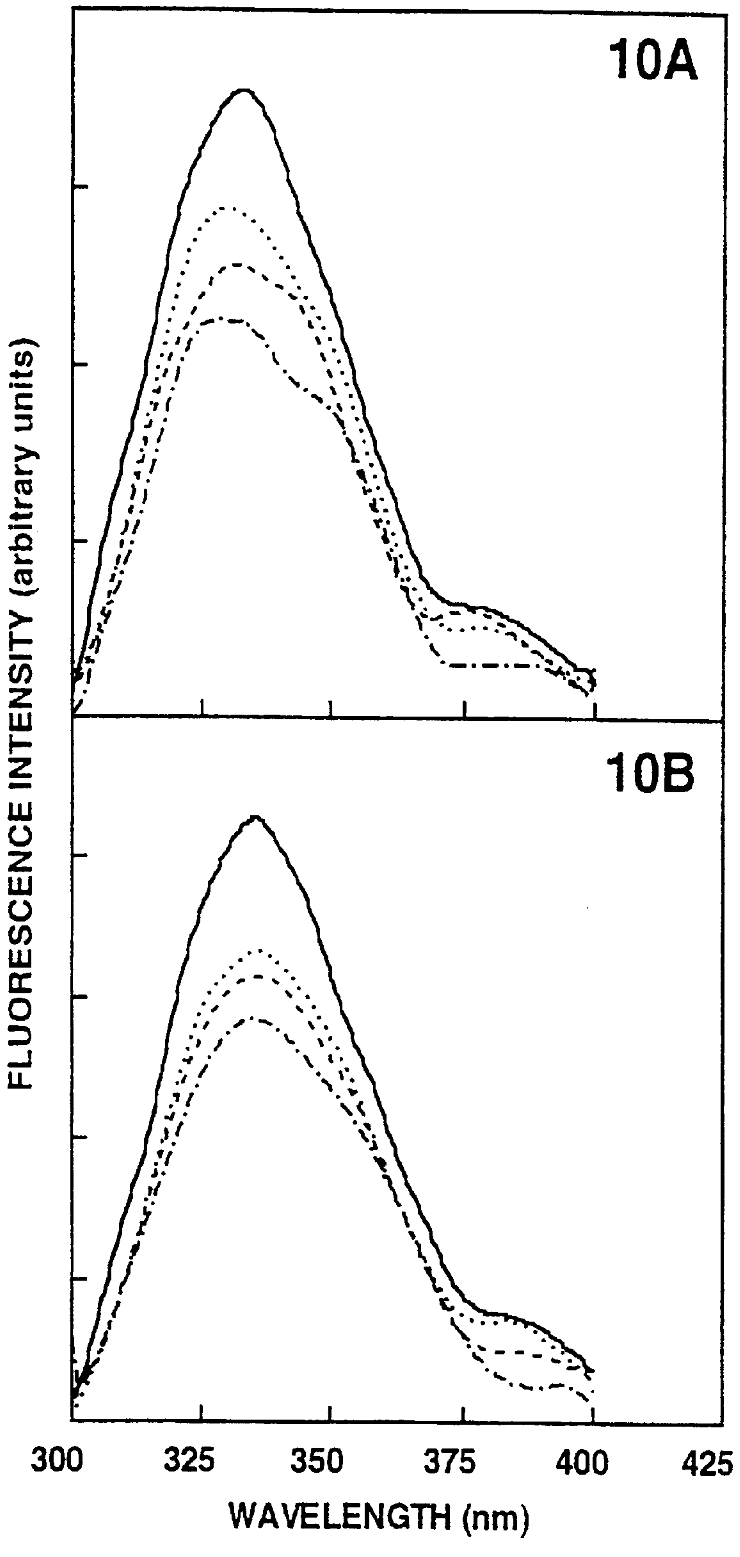
FIGS. 10A–B show quenching of the environmentally sensitive tryptophan by brominated phospholipids. Melittin (FIG. 10A) and [D]-$V^{5,8}$,$I^{17}$,$K^{21}$-melittin (10B) were added to buffer containing PC/PS (1:1 w/w) SUV. The SUV contained 25% of either 6,7 Br-PC (—·—·—·—), or 9,10 Br-PC ( - - - ), or 11,12 Br-PC ( . . . ). After 2 min incubation, an emission spectrum of the tryptophan was recorded using spectrofluorometer with excitation set at 280 nm. For comparison PC/PS (1:1 w/w) SUV with no Br-PC were used (——).

2.6 Tryptophan Quenching Experiments. A tryptophan residue naturally present in the sequence of a protein or a peptide can serve as an intrinsic probe for the localization of the peptide within a membrane. Melittin contains a tryptophan residue at position 19, the N-terminal side of the C-helix. With both melittin and peptide 18, the largest quenching of tryptophan fluorescence was observed with 6,7-Br-PC/PS vesicles (FIG. 10). Less quenching was observed with 9,10-Br-PC/PS, and the least with 11,12-Br-PC/PS. These results indicate that upon binding to vesicles, the peptides were located near the head groups of the phospholipids.

EXAMPLE 3

Synthesis and Biological Activity of Model Lys/Leu Diastereomers 3.1 Lys/Leu diastereomers design. Six diastereomers of short linear model 12-mer peptides composed of varying ratios of lysine and leucine were synthesized in order (1) to examine whether a balance between hydrophobicity and a net positive charge may be a sufficient criteria necessary for selective bacterial lysis, and (2) to gain insight into the mechanism underlying this effect.

In the first series of model Lys/Leu 12-mer peptides 22–25, one third of their sequence was composed of D-amino acid residues. The location of the D-amino acids remained constant in all peptides which was constructed for maximum disruption of α-helical structure. D-amino acids were distributed along the peptide, leaving only very short stretches of 1–3 consecutive L-amino acids. The following peptides were synthesized:

22. [D]-$L^{3,4,8,10}$-$K_3L_9$ of the sequence:

Lys-Leu-Leu-Leu-Leu-Leu-Lys-Leu-Leu-Leu-Leu-Lys-$NH_2$

23. [D]-$L^{3,4,8,10}$-$K_4L_8$, of the sequence

Lys-Leu-Leu-Leu-Lys-Leu-Leu-Leu-Lys-Leu-Leu-Lys-$NH_2$

24. [D]-$L^{3,4,8,10}$-$K_5L_7$, of the sequence

Lys-Leu-Leu-Leu-Lys-Leu-Lys-Leu-Lys-Leu-Leu-Lys-$NH_2$

25. [D]-$L^{3,4,8,10}$-$K_7L_5$ of the sequence:

Lys-Lys-Leu-Leu-Lys-Leu-Lys-Leu-Lys-Leu-Lys-Lys-$NH_2$

In the second series of model Lys/Leu 12-mer peptides 26–27, two thirds of their sequence were composed of D-amino acid residues, at the exact positions of the L-amino acid residues of peptides 23 and 24 as follows:

26. [D]-$K^{1,5,9,12}L^{2,6,7,11}$-$K_4L_8$, of the sequence:

Lys-Leu-Leu-Leu-Lys-Leu-Leu-Leu-Lys-Leu-Leu-Lys-$NH_2$

27. [D]-$K^{1,5,7,9,12}L^{2,6,11}$-$K_5L_7$, of the sequence:

Lys-Leu-Leu-Leu-Lys-Leu-Lys-Leu-Lys-Leu-Leu-Lys-$NH_2$

In a third series of model Lys/Leu peptides. a 6-mer and a 8-mer diastereomers were synthesized (peptides 28 and 29, respectively):

28. [D]-$L^{1,3}$-$K_2L_4$, of the sequence:

Lys-Leu-Leu-Leu-Leu-Lys

29. $L^{2,4,6}$-$K_3L_5$ of the sequence:

Lys-Leu-Leu-Leu-Lys-Leu-Leu-Lys

Further Lys/Leu diastereomers according to the invention that were synthesized:

30. Lys Leu Leu Leu Lys Leu Lys Leu Lys Leu Leu Lys

31. Lys Leu Leu Leu Lys Leu Lys Leu Lys Leu Leu Lys

32. Lys Leu Leu Leu Lys Leu Lys Leu Lys Leu Leu Lys 3.2 Synthesis of Lys/Leu diastereomers—The peptides were synthesized as described in Experimental Procedures, section (ii). The peptides were then characterized with regard to their structure, biological function and interaction with bacteria and model membranes composed of either zwitterionic or negatively charged phospholipids.

Figure 11:
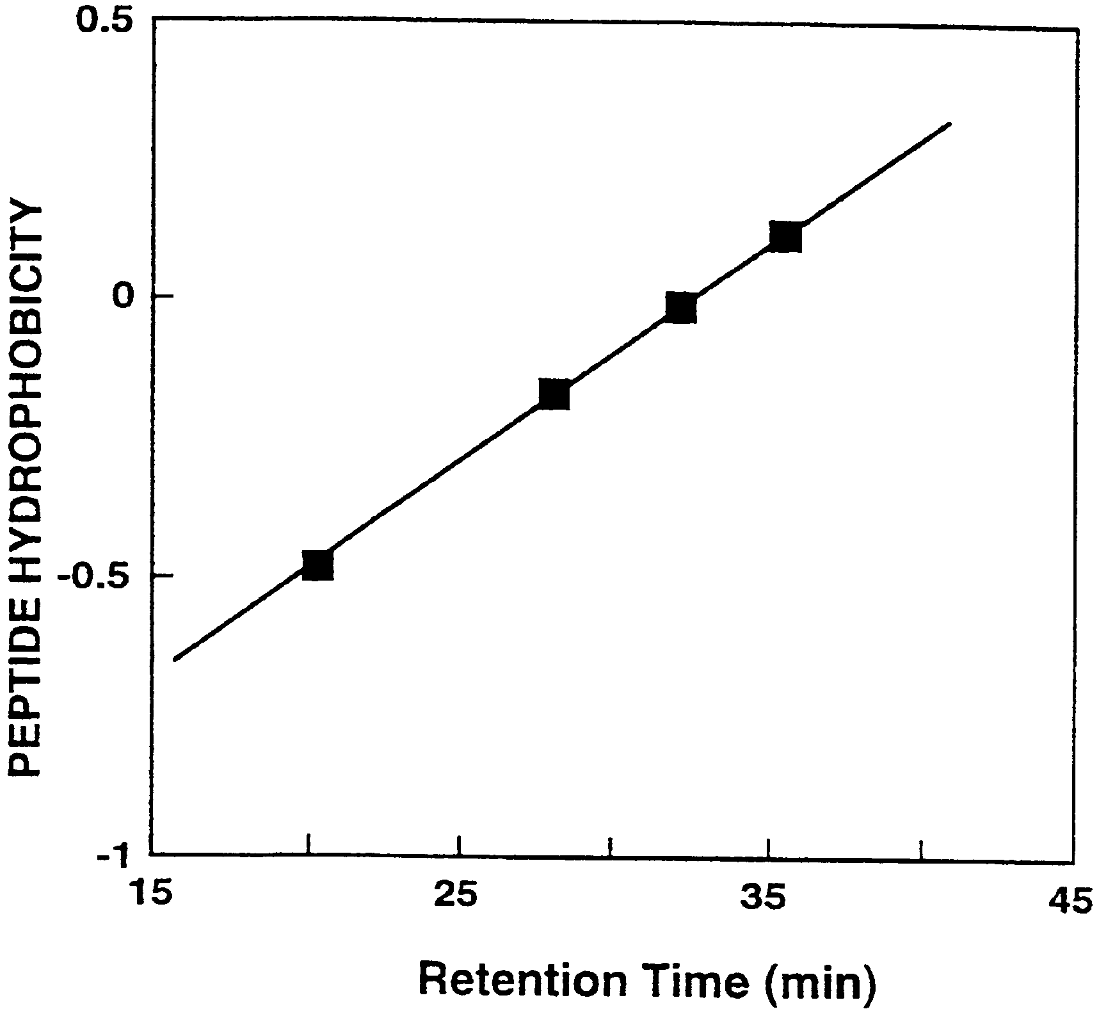
FIG. 11 shows the effect of the hydrophobicity of the Leu/Lys diastereomers on RP-HPLC retention time.

3.3 Hydrophobicity. The hydrophobicities and net positive charges of the peptides 22–25 are listed in Table 4. Mean values of hydrophobicity were calculated using consensus value of hydrophobicity scale (Eisenberg et al., 1984). As shown in FIG. 11, a direct correlation was found between hydrophobicity and the retention time of the peptides, suggesting that structure does not significantly contribute to overall hydrophobic interactions with the stationary phase.

TABLE 4

Hydrophobicity and net charge of the Leu/Lys diastereomers.

| Peptide Designation | Net Charge | Hydrophobicity |
|---|---|---|
| 22. | +4 | 0.12 |
| 23. | +5 | −0.01 |
| 24. | +6 | −0.15 |
| 25. | +8 | −0.42 |

3.4 CD spectroscopy. The extent of the α-helical structure of the diastereomers 22–25 was determined from their CD spectra in 40% TFE. As expected, after incorporation of D-amino acids, no signal was observed for all the diastereomers, demonstrating the lack of any specific secondary structure (data not shown). It is to be noted that in a recent study, a peptide with a sequence identical to that of peptide 23, but composed of only L-amino acids, was found to have about 40% α-helical structure in methanol and in DMPC vesicles (Cornut et al., 1994).

Figure 12:
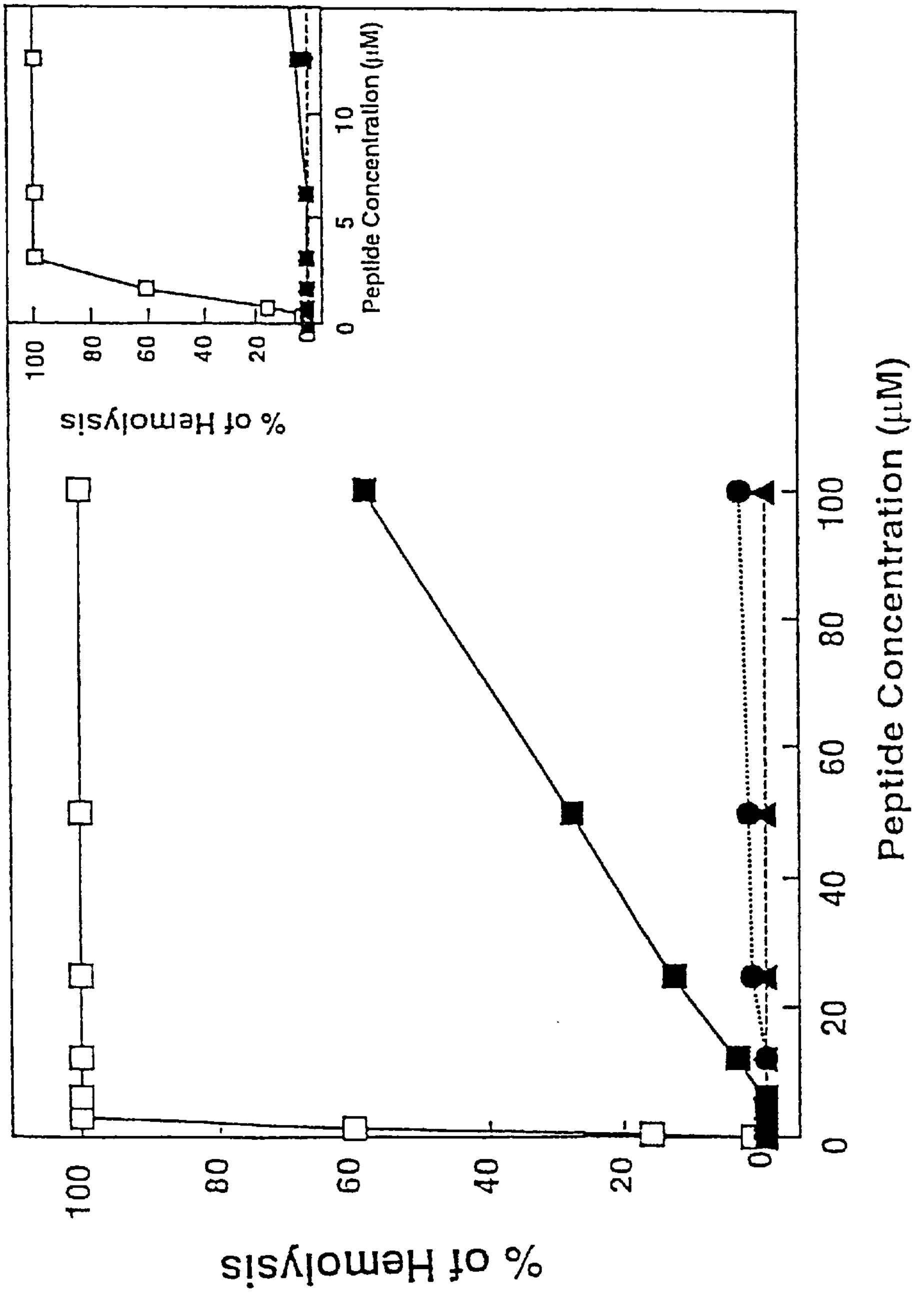
FIG. 12 shows dose-response curves of the hemolytic activity of the Leu/Lys diastereomers towards hRBC. The inset shows the assay results at low concentrations. Symbols: empty squares, melittin; filled squares, [D]-$L^{3,4,8,10}$-$K_3$ Lg; filled circles, [D]-$L^{3,4,8,10}$-$K_4L_8$; empty triangles, [D]-$L^{3,4,8,10}$-$K_5L_7$; filled triangles, [D]-$L^{3,4,8,10}$-$K_7L_5$.

3.5 Antibacterial and hemolytic activity of the peptides 22–29. The hemolytic activity of the peptides 22–29 against hRBC was tested. A dose response curve for the hemolytic activity of the peptides 22–25 is shown in FIG. 12 wherein the hemolytic activity of melittin served as a control. A direct correlation was found between the hydrophobicity (Table 4) and the hemolytic activity of the diastereomers. Peptide 22, [D]-$L^{3,4,8,10}$-$K_3L_9$, which has the highest hydrophobicity, was the most hemolytic peptide. However, its hemolytic activity is very low in comparison to melittin (>60 fold less activity). All the other peptides showed no significant hemolytic activity up to the maximum concentration tested (100 μM). The hemolytic activity of peptides 22–29 is shown in Table 5. It should be noted that although peptide 23, [D]-$L^{3,4,8,10}$-$K_4L_8$, is not hemolytic at concentrations >100 fold of those required for significant hemolysis by melittin, its entirely L-amino acid form has been shown in a recent study to have hemolytic activity similar to that of melittin (~5 fold less) (Cornut et al., 1994).

The peptides 22–29 were also tested for their antibacterial activity against a representative set of bacteria, in which tetracycline, dermaseptin S, and melittin served as controls. The resultant MICs are shown in Table 5. The data show that the antibacterial activity of the diastereomers 22–29 was modulated by the balance between hydrophobicity and positively charged amino acids. Both the most hydrophobic peptide 22 and the most hydrophilic peptide 25 displayed the lowest range in antibacterial activity (Table 5). However, peptides 23 and 24 displayed high antibacterial activity against most of the bacteria tested with the former being slightly more potent. Furthermore, each peptide had a unique spectrum of antibacterial activity, and each was active more against Gram-positive as compared to Gram-negative bacteria.

3.6 Synergistic effects between tetracycline and the Lys/Leu diastereomers in serum. To investigate a possible synergistic relationship between the antibiotic tetracycline and the diastereomers, tetracycline was tested in 2-fold serial dilutions against *Pseudomonas aeruginosa* (ATCC 27853) in the presence of a constant equimolar concentration (1 μM) of peptide 24, [D]-$L^{3,4,8,10}$-$K_5L_7$. Antibacterial activity of the mixtures was determined as described in Experimental procedures, section (xii).

A synergistic effect was observed between tetracycline and the diastereomer 24. Tetracycline shows little activity against *P. aeruginosa*. However, when mixed with 1 μM solution of peptide 24, a concentration which is 10 fold lower than that required for lytic activity against *P. aeruginosa,* an eight fold increase in the activity of tetracycline was observed (Table 6). A possible explanation for the synergistic effect is that the peptide slightly disrupts the bacterial wall which improves partitioning of tetracycline into the bacteria. This is supported by electron microscopy studies which show that below its MIC, peptide 24 causes morphological changes in the bacterial wall (FIG. 14). In addition, the effect of pooled human serum on the antibacterial activity of peptide 24 and the native antibacterial peptide dermaseptin against *P. aeruginosa* and *E. coli* was found to differ considerably (Table 6). While dermaseptin was 8–10 fold less active in the presence of serum, peptide 24 retained its antibacterial activity.

pholipid vesicles. Furthermore, the ability of the peptides to permeate PE/PG vesicles correlates with the antibacterial activity of the peptides against *E. coli* (Table 5). Peptide 25, which has the lowest antibacterial activity, also had significantly decreased ability to permeate PE/PG vesicles compared to the other three peptides 22–24.

3.8 Electron microscopy study of bacterial lysis. The effect of the diastereomers 22–25 on the morphology of treated *E. coli* was visualized using transmission electron microscopy. All the peptides caused total lysis of the bacteria at the MIC (data not shown). However, when the peptides were utilized at concentrations corresponding to 80% of their MIC, some differences in the morphology of the treated bacteria were observed, depending upon the peptide used.

TABLE 5

Minimal Inhibitory Concentration (μM) of the peptides.

| Peptide Designation | Minimal Inhibitory Concentration[a] (μM) *E. Coli* (D21) | *A. calcoaceticus* (Ac11) | *P. aeruginosa* (ATCC-27853) | *B. megaterium* (Bm11) | *B. subtilis* (ATCC-6051) | % Hemolysis at 100 μM |
|---|---|---|---|---|---|---|
| 22 | 9 | 20 | 125 | 0.7 | 1.1 | 58 |
| 23 | 3.5 | 4 | 10 | 0.4 | 0.5 | 0 |
| 24 | 7 | 20 | 10 | 0.25 | 2 | 0 |
| 25 | 80 | 200 | >200 | 1 | 100 | 0 |
| 26 | 4 | N.D | N.D | 0.5 | N.D | 0 |
| 27 | 7 | N.D | N.D | 0.2 | N.D | 0 |
| 28 | 200 | N.D | N.D | 50 | N.D | 0 |
| 29 | 3 | N.D | N.D | 3 | N.D | 0 |
| Dermaseptin S | 6 | 3 | 25 | 0.5 | 4 | — |
| Melittin | 5 | 2 | 25 | 0.3 | 0.6 | — |
| Tetracycline | 1.5 | 1.5 | 50 | 1.2 | 6.5 | — |

[a]Results are the mean of 3 independent experiments each performed in duplicates, with standard deviation of 20%

TABLE 6

Minimal Inhibitory Concentration (μM)[a] in the presence of human serum and synergistic activity of peptide 24

| | Minimal Inhibitory Concentration (μM) | | | |
|---|---|---|---|---|
| | *P. aeruginosa* (ATCC-27853) | | *E. coli* (D21) | |
| Peptide Designation | 0% Serum | 33% Serum | 0% Serum | 33% Serum |
| 24 | 10 | 10 | 7 | 7 |
| Dermaseptin S | 25 | 200 | 6 | 50 |
| Tc[b] | 50 | | | |
| Tc + 24 (1 μM) | 6 | | | |

Figure 13:
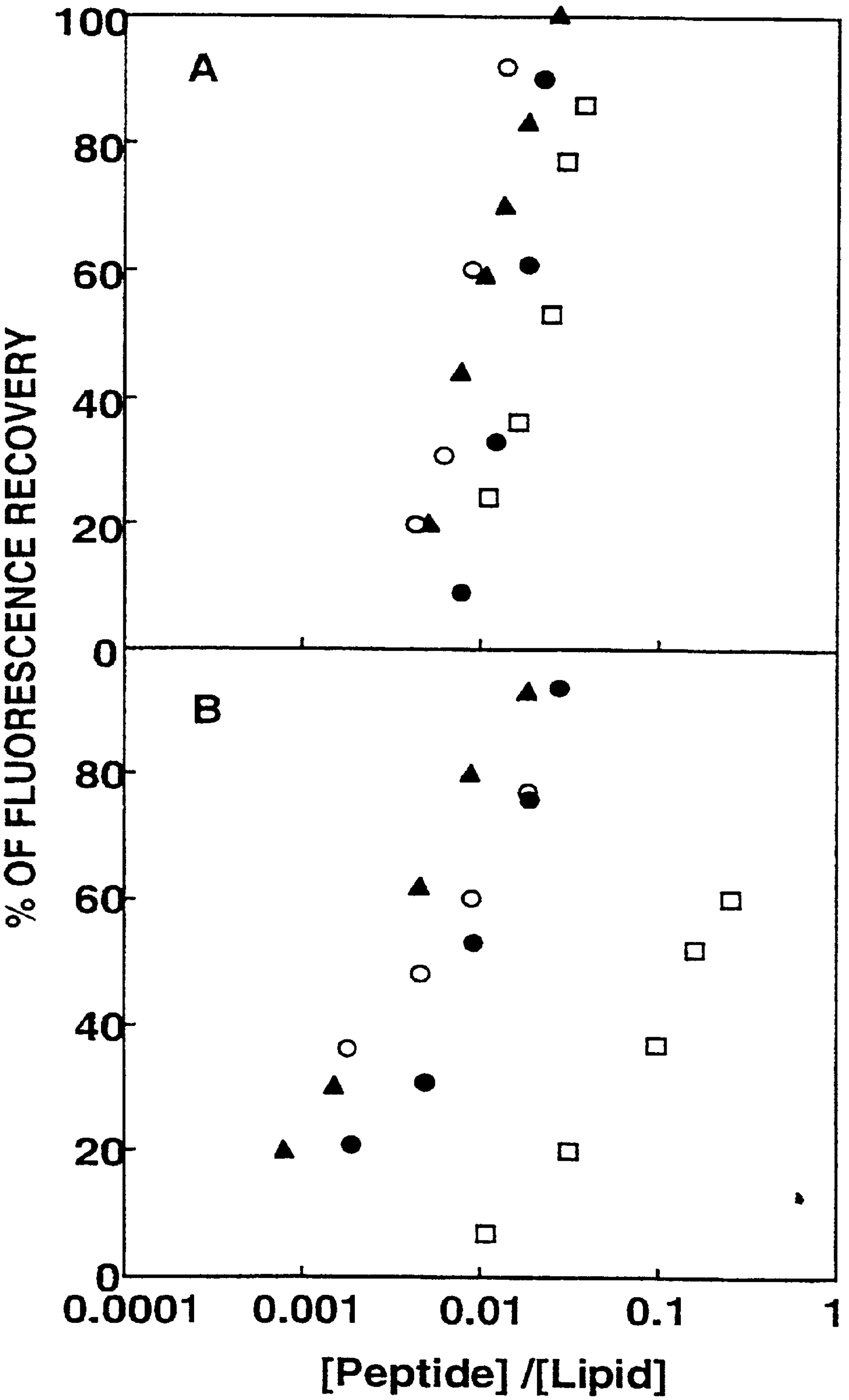
FIGS. 13A–B show maximal dissipation of the diffusion potential in vesicles, induced by the Leu/Lys diastereomers . The peptides were added to isotonic $K^+$ free buffer containing SUV composed of PC (FIG. 13A) or PE/PG (13B), pre-equilibrated with the fluorescent dye diS-$C_2$-5 and valinomycin. Fluorescence recovery was measured 3–10 min after the peptides were mixed with the vesicles. Symbols: filled squares, [D]-$L^{3,4,8,10}$-$K_3L_9$; filled circles, [D]-$L^{3,4,8,}$ 10-$K_4L_8$; filled triangles, [D]-$L^{3,4,8,10}$-$K_5L_7$; crossed circles, [D]-$L^{3,4,8,10}$-$K_7L_5$.

[a]·Results are the mean of 2 independent experiments each performed in duplicates, with standard deviation of 20%.
[b]·Tc - Tetracycline 3.7 Peptide-induced membrane permeation. Various concentrations of peptides were mixed with vesicles that had been pretreated with the fluorescent dye, diS-$C_2$-5, and valinomycin. The kinetics of the fluorescence recovery was monitored and the maximum fluorescence level was determined as a finction of peptide concentration (FIG. 13). PC/cholesterol vesicles (10:1) served as a model of the phospholipid composition of the outer erythrocyte leaflet (Verkleij et al., 1973), and PE/PG vesicles (7:3) was used to mimic the phospholipid composition of E. coli (Shaw, 1974). A direct correlation was found between the potential of the peptides to permeate model phospholipid membranes and their lytic activity against erythrocytes and *E. coli.* Only the hemolytic peptide 22 permeated the zwitterionic phos- The most hydrophobic peptide 22 caused the most damage to the cell wall and membranes, while the least hydrophobic peptide 25 only caused local perturbations (FIG. 14).

EXAMPLE 4

Synthesis and Biological Activity of Model Lys/Ala and Lys/Val Diastereomers 4.1 Diastereomer design. To further examine whether modulating hydrophobicity and the net positive charge of linear cytotoxic peptides is sufficient to confer selective antibacterial activity, two further model 12-mer peptides 33 and 34–37, composed of Lys/Ala or Lys/Val residues, respectively, with at least one third of their sequences being of D-Ala or D-Val residues, were synthesized:

33. [D]-$A^{3,4,8,10}$-$K_4A_8$ of the sequence:

Lys-Ala-Ala-Ala-Lys-Ala-Ala-Ala-Lys-ALa-Ala-Lys-$NH_2$

34. [D]-$V^{3,4,8,10}$-$K_4V_8$ of the sequence:
Lys-Val-Val-Val-Lys-Val-Val-Val-Lys-Val-Val-Lys-$NH_2$
35. Lys Val Val Val Lys Val Lys Val Lys Val Val Lys
36. Lys Val Val Val Lys Val Lys Val Lys Val Val Lys
37. Lys Val Val Val Lys Val Lys Val Lys Val Val Lys 4.2 Synthesis. The Lys/Ala and Lys/Val diastereomers were synthesized as described in Experimental Procedures, section (ii).

4.3 Antibacterial and hemolytic activity. Peptides 33 and 34 were tested against *E. coli* and *B. megaterium* and hRBC.

The results in Table 7 show that both model diastereomers are antibacterial and non-hemolytic:

TABLE 7

Minimal Inhibitory Concentration (μM) and hemolytic activity of the peptides 28 and 29

| Peptide Designation | Minimal Inhibitory Concentration (LLM) E. coli (D21) | B. megaterium (Bm11) | % hemolysis at 100 μM |
|---|---|---|---|
| 33 | 12 | 1 | 0 |
| 34 | 3.5 | 0.8 | 0 |

EXAMPLE 5

Synthesis of Further Model Diastereomers

The following model diastereomers according to the invention composed of sequences of 6, 8, 12, 14, 16, 19, 25, 26 and 30 residues of two, three or more different amino acids, were synthesized:

38. Lys Leu Ile Leu Lys Leu

39. Lys Val Leu His Leu Leu

40. Leu Lys Leu Arg Leu Leu

41. Lys Pro Leu His Leu Leu

42. Lys Leu Ile Leu Lys Leu Val Arg

43. Lys Val Phe His Leu Leu His Leu

44. His Lys Phe Arg Ile Leu Lys Leu

45. Lys Pro Phe His Ile Leu His Leu

46. Lys Ile Ile Ile Lys Ile Lys Ile Lys Ile Ile Lys

47. Lys Ile Ile Ile Lys Ile Lys Ile Lys Ile Ile Lys

48. Lys Ile Ile Ile Lys Ile Lys Ile Lys Ile Ile Lys

49. Lys Ile Pro Ile Lys Ile Lys Ile Lys Ile Pro Lys

50. Lys Ile Pro Ile Lys Ile Lys Ile Lys Ile Val Lys

51. Arg Ile Ile Ile Arg Ile Arg Ile Arg Ile Ile Arg

52. Arg Ile Ile Ile Arg Ile Arg Ile Arg Ile Ile Arg

53. Arg Ile Ile Ile Arg Ile Arg Ile Arg Ile Ile Arg

54. Arg Ile Val Ile Arg Ile Arg Ile Arg Leu Ile Arg

55. Arg Ile Ile Val Arg Ile Arg Leu Arg Ile Ile Arg

56. Arg Ile Gly Ile Arg Leu Arg Val Arg Ile Ile Arg

57. Lys Ile Val Ile Arg Ile Arg Ile Arg Leu Ile Arg

58. Arg Ile Ala Val Lys Trp Arg Leu Arg Phe Ile Lys

59. Lys Ile Gly Trp Lys Leu Arg Val Arg Ile Ile Arg

60. Lys Lys Ile Gly Trp Leu Ile Ile Arg Val Arg Arg

61. Arg Ile Val Ile Arg Ile Arg Ile Arg Leu Ile Arg Ile Arg

62. Arg Ile Ile Val Arg Ile Arg Leu Arg Ile Ile Arg Val Arg

63. Arg Ile Gly Ile Arg Leu Arg Val Arg Ile Ile Arg Arg Val

64. Lys Ile Val Ile Arg Ile Arg Ala Arg Leu Ile Arg Ile Arg Ile Arg

65. Arg Ile Ile Val Lys Ile Arg Leu Arg Ile Ile Lys Lys Ile Arg Leu

66. Lys Ile Gly Ile Lys Ala Arg Val Arg Ile Ile Arg Val Lys Ile Ile

67. Arg Ile Ile Val His Ile Arg Leu Arg Ile Ile His His Ile Arg Leu

68. His Ile Gly Ile Lys Ala His Val Arg Ile Ile Arg Val His Ile Ile

69. Arg Ile Tyr Val Lys Ile His Leu Arg Tyr Ile Lys Lys Ile Arg Leu

70. Lys Ile Gly His Lys Ala Arg Val His Ile Ile Arg Tyr Lys Ile Ile

71. Arg Ile Tyr Val Lys Pro His Pro Arg Tyr Ile Lys Lys Ile Arg Leu

72. Lys Pro Gly His Lys Ala Arg Pro His Ile Ile Arg Tyr Ile Ile

73. Lys Ile Val Ile Arg Ile Arg Ile Arg Leu Ile Arg Ile Arg Ile Arg Lys Ile Val

74. Arg Ile Ile Val Lys Ile Arg Leu Arg Ile Ile Lys Lys Ile Arg Leu Ile Lys Lys

75. Lys Ile Gly Trp Lys Leu Arg Val Arg Ile Ile Arg Val Lys Ile Gly Arg Leu Arg

76. Lys Ile Val Ile Arg Ile Arg Ile Arg Leu Ile Arg Ile Arg Ile Arg Lys Ile Val Lys Val Lys Arg Ile Arg

77. Arg Phe Ala Val Lys Ile Arg Leu Arg Ile Ile Lys Lys Ile Arg Leu Ile Lys Lys Ile Arg Lys Arg Val Ile Lys

78. Lys Ala Gly Trp Lys Leu Arg Val Arg Ile Ile Arg Val Lys Ile Gly Arg Leu Arg Lys Ile Gly Trp Lys Lys Arg Val Arg Ile Lys

79. Arg Ile Tyr Val Lys Pro His Pro Arg Tyr Ile Lys Lys Ile Arg Leu

80. Lys Pro Gly His Lys Ala Arg Pro His Ile Ile Arg Tyr Lys Ile Ile

81. Lys Ile Val Ile Arg Ile Arg Ile Arg Leu Ile Arg Ile Arg Ile Arg Lys Ile Val

82. Arg Ile Ile Val Lys Ile Arg Leu Arg Ile Ile Lys Lys Ile Arg Leu Ile Lys Lys

83. Arg Ile Tyr Val Ser Lys Ile Ser Ile Tyr Ile Lys Lys Ile Arg Leu

84. Lys Ile Val Ile Phe Thr Arg Ile Arg Leu Thr Ser Ile Arg Ile Arg Ser Ile Val

85. Lys Pro Ile His Lys Ala Arg Pro Thr Ile Ile Arg Tyr Lys Met Ile

EXAMPLE 6

Synthesis and Biological Activity of Cyclic Diastereomers 6.1 Design. The following cyclic derivatives of diastereomers of pardaxin fragments with cysteine residues at both the N- and C-termini were synthesized:

86. Cyclic $K^{1}[D]P^{7}L^{18}L^{19}$[1–22]-par of the sequence:

Cys-Lys-Gly-Phe-Phe-Ala-Leu-Ile-Pro-Lys-Ile-Ile-Ser-

Ser-Pro-Leu-Phe-Lys-Thr-Leu-Leu-Ser-Ala-Val-Cys

87. Cyclic $K^{1}K^{2}[D]P^{7}L^{18}L^{19}$[1–22]-par of the sequence:

Cys-Lys-Lys-Gly-Phe-Phe-Ala-Leu-Ile-Pro-Lys-Ile-Ile-Ser

Ser-Pro-Leu-Phe-Lys-Thr-Leu-Leu-Ser-Ala-Val-Cys

88. Cyclic $K^1K^2K^3$[D]$P^7L^{18}L^{19}$[1–22]-par of the sequence:

Cys-Lys-Lys-Lys-Gly-Phe-Phe-Ala-Leu-Ile-Pro-Lys-Ile-Ile-
Ser-Ser-Pro-Leu-Phe-Lys-Thr-Leu-Leu-Ser-Ala-Val-Cys

The following cyclic derivatives of diastereomers of different amino acid residues with cysteine residues at both the N- and C-termini were synthesized:

89. Cyclic Cys Arg Ile Val Ile Arg Ile Arg Ile Arg Leu Ile Arg Ile Arg Cys

90. Cyclic Cys Lys Pro Gly His Lys Ala Arg Pro His Ile Ile Arg Tyr Lys Ile Ile Cys 91. Cyclic Cys Arg Phe Ala Val Lys Ile Arg Leu Arg Ile Ile Lys Lys Ile Arg Leu Ile Lys Lys Ile Arg Lys Arg Val Ile Lys Cys 6.2 Synthesis of the cyclic diastereomers. The cyclic peptides were synthesized by a solid-phase method as described in Experimental Procedures, section (ii), with cysteine residues at both the N and C-termini of the peptides. After HF cleavage and RP-HPLC purification the peptides were solubilized at low concentration in PBS (pH 7.3), and cyclization was completed after 12 h. The cyclic peptides were farther purified on RP-HPLC and subjected to amino acid analysis to confirm their composition, and SDS-PAGE to confirm their monomeric state.

6.3 Antibacterial and hemolytic activity. Peptides 86–88 were tested against *E. coli* and *B. megaterium* and HRBC. The results in Table 8 show that all three cyclic pardaxin-derived diastereomers are antibacterial and non-hemolytic:

TABLE 8

Minimal Inhibitory Concentration (μM) and hemolytic activity of the cyclic pardaxin-derived diastereomers.

| Peptide Designation | Minimal Inhibitory Concentration (μM) *E. coli* (D21) | *B. megaterium* (Bm11) | % hemolysis at 100 μM |
|---|---|---|---|
| 86 | 30 | 10 | 0 |
| 87 | 15 | 6 | 0 |
| 88 | 7.5 | 2 | 0 |

EXAMPLE 7

Synthesis and Biological Activity of Bundled Lys/Leu Peptide Diastereomers 7.1 Design. Using as template peptide 23 and as monomers peptide 23 or 24 with an additional cysteine residue at the C-terminus (23C and 24C, respectively, the following bundle-sequences were produced:

92. ([D]-$L^{3,4,8,10}$-$K_4L_8C)_5$ [D]-$L^{3,4,8,10}$-$K_4L_8$ of the sequence:

(Lys-Leu-Leu-Leu-Lys-Leu-Leu-Leu-Lys-Leu-Leu-Lys-Cys-$NH_2)_5$ Lys-Leu-Leu-Leu-Lys-Leu-Leu-Leu-Lys-Leu-Leu-Lys-$NH_2$ 93. ([D]-$L^{3,4,8,10\text{-}K}{}_5L_7C)_5$ [D]-$L^{3,4,8,10}$-$K_4L_9$ of the sequence:

(Lys-Leu-Leu-Leu-Lys-Leu-Lys-Leu-Lys-Leu-Leu-Lys-Cys-$NH_2)_5$ Lys-Leu-Leu-Leu-Lys-Leu-Leu-Leu-Lys-Leu-Leu-Lys-$NH_2$ 7.2 Synthesis. In order to produce template-bound diastereomers, 1:1 molar ratio of DCC and bromoacetic acid were allowed to react in DMSO at 25° C. for 1 h. The template (peptide 23) was added to the reaction mixture and left under agitation for 12 h after which the DMSO was lyophilized. The remaining bromoacetic acid was extracted with dry ether. The template was then reacted with excess of diastereomers 23C and 24C with cysteine residue at their C-terminus, in PBS pH 7.3 at 25° C. for 1 h. The template-bound diastereomers 92 and 93 were further purified on RP-HPLC, and examined on SDS-PAGE to confirm their aggregation state.

7.3 Antibacterial and hemolytic activity. The template-bound diastereomers diastereomers 92 and 93 were tested against *E. coli* and *B. megaterium* and hRBC. The results in Table 9 show that both bundle sequences are antibacterial and non-hemolytic.

TABLE 9

Minimal Inhibitory Concentration (μM) and hemolytic activity of the bundles.

| Peptide Designation | Minimal Inhibitory Concentration (μM) *E. Coli* (D21) | *B. megaterium* (Bm11) | % hemolysis at 100 μM |
|---|---|---|---|
| 92 | 0.2 | 0.05 | 0 |
| 93 | 0.1 | 0.02 | 0 |

EXAMPLE 8

Synthesis and Biological Activity of Mixtures of Water-soluble Lys/Leu 12-mer peptide diastereomers Peptides were synthesized by a solid phase method as described in Experimental Procedures, section (ii) above. At each coupling step a mixture composed of 1 eq each of lysine, leucine and D-leucine was added to the reaction. The synthesis resulted in a mixture of $3^{12}$ different peptides. After HF cleavage the water-soluble peptides were extracted with double distilled water (ddw) and lyophilized.

The water-soluble mixture of the Lys/Leu 12-mer peptide diastereomers was tested against *E. coil* D21 (MIC: 15 μg/ml) and *B. megaterium* Bml1 D21 (MIC: 3 μg/ml) and HRBC (0% hemolysis at 100 μM). As expected, the water-soluble mixture had antibacterial activity but was non-hemolytic.

EXAMPLE 9

Synthesis and Biological Activity of Lys/Leu/D-Leu Random Copolymers

In order to produce diastereomers of polymers of different sizes, excess of N-carboxyanhydride residues over initiator free amino acids were allowed to polymerize in DMF at 25° C. for 4 h (Katchalski and Sela, 1958). Polymers consisting of different ratios of lysine, leucine and D-leucine were produced using different ratios of lysine-N-carboxyanhydride, leucine-N-carboxyanhydride and D-leucine-N-carboxyanhydride. Three of such polymers and their antibacterial and hemolytic activity are shown in Table 10.

TABLE 10

Minimal Inhibitory Concentration ($\mu$M) and hemolytic activity of the Lys/Leu/D-Leu copolymers.

| Amino Acids Ratio (Molar) Lys: Leu: [D]-Leu | Minimal Inhibitory Concentration ($\mu$g/ml) *E. coli* (D21) | megaterium (Bm11) | % hemolysis at 100 $\mu$M |
|---|---|---|---|
| 1:1:1 | 90 | 15 | 0 |
| 2:1:1 | 35 | 8 | 0 |
| 3:1:1 | 80 | 20 | 0 |

EXAMPLE 10

Antifungal Activity of the Diastereomers

The antifungal activity of the pardaxin-derived peptides 1 and 16 (see Example 1 above) was examined in sterile 96-well plates (Nunc F96 microtiter plates) in a final volume of 100 $\mu$L as follows: Fifty microliters of a suspension containing fungi at concentration of $1\times10^6$ Colony-Forming Units (CFU)/ml in culture medium (Sabouraud's glucose broth medium) was added to 50 $\mu$L of water containing the peptide in serial 2-fold dilutions in water. Inhibition of growth was determined by measuring the absorbance at 492 nm with a Microplate autoreader El309 (Bio-tek Instruments), after an incubation time of 48 h at 30° C. Antifingal activities were expressed as the minimal inhibitory concentration (MIC), the concentration at which 100% inhibition of growth was observed after 48 h of incubation. The fungi used were: *Candida albicans* (IP886-65) and *Cryptococcus neoformans* (IP960-67). As shown in

TABLE 11

Minimal Inhibitory Concentration ($\mu$M) of tbe diastereomers 1 and 16 against fungi

| Peptide Designation | Minimal Inhibitory Concentration ($\mu$M) *Candida albicans* (IP886-65) | Cryptococcusneoformans (IP960-67) |
|---|---|---|
| 1 | 35 | 50 |
| 16 | 120 | 150 |

EXAMPLE 11

Anticancer Activity of the Diastereomers

The anticancer activity of the Lys/Leu diastereomers 23 and 24 (see Example 3 above) was examined against mouse adenocarcinoma. Cells were seeded at 5–10 000/well in 96-well microtiter plates in Dulbecco s modified Eagle's medium. After the cells had attached, 20 $\mu$l of diluted peptide solution in normal saline were transferred to the well to give final concentrations ranging from 20 to 150 $\mu$M. Following lh incubation with the peptides, the viability of the cancer cell was measured by Trypan blue (0.1% w/v) vital staining assay. In control experiments the peptide solvent alone was added to the cells. Anticancer activities were expressed as the minimal inhibitory concentration (MIC), the concentration at which 100% inhibition of growth was observed after 1 h of incubation. The results in Table 12 show that both peptides are active against malignant cells.

TABLE 12

Minimal Inhibitory Concentration ($\mu$M) of the diastereomers against mouse adenocarcinoma.

| Peptide Designation | Minimal Inhibitory Concentration ($\mu$M) mouse adenocarcinoma |
|---|---|
| 23 | 50 |
| 24 | 80 |

EXAMPLE 12

Activity of the Diastereomers Against *Leishmania mexicana*

The melittin-derived diastereomer peptide 20 (see Example 2 above) and the Leu/Lys diastereomer peptide 23 (see Example 3 above) were tested against Leishmania. Promastigotes of the *Leishmania mexicana* NR strain to be assayed were cultured at 27° C. in RPMI 1640 medium supplemented with 10% fetal bovine serun. Parasite were harvested by centrifugation at 1200×g for 10 min at 4° C. and washed twice with PBS (50 mM sodium phosphate, 150 mM NaCl, pH 7). The washed promastigotes were counted in a hemocytometer and adjusted to $1\times10^6$ parasites/ml. Aliquotes of this suspension were assayed in a final volume of 100 $\mu$l by counting living (motile) cells after 24 h of incubation at 26° C. in the absence or presence of various concentrations of the diastereomers. Anti -Leishmania activities were expressed as the minimal inhibitory concentration (MIC), the concentration at which 100% death was observed after 24 h of incubation. It was found that for peptide 23 the MIC is 17 $\mu$M and for peptide 20 the MIC is 32 $\mu$M.

EXAMPLE 13

Antiviral Activity of the Diastereomer 23

Sendai virus (Z strain) was grown in the allantoic sac of 10–11 day old embryonated chicken eggs, harvested 48 h after injection and purified. The virus was resuspended in buffer composed of 160 mM NaCl, 20 mM tricine, pH 7.4, and stored at −70 ° C. Virus haemagglutinating activity was measured in haemagglutinating units (HAU). One microlitre contained 60000 HAU. Fresh human blood was obtained from a blood bank and stored for up to 1 month at 4° C. Prior to use, erythrocytes were washed twice with PBS pH 7.2, and diluted to the desired concentration (% v/v) with the same buffer. Virions, erythrocytes and peptides were mixed in different orders of addition and various amounts. The final incubation was always at 37° C. for 60 min, followed by centrifugation at 5700 g for 10 min to remove intact cells. In all cases duplicate samples were used and two aliquots were taken from the supernatant of each sample to two wells of a 96-well plate. The amount of hemoglobin release was monitored by measuring the absorbance of the wells with the ELISA plate reader at 540 nm. Antiviral activity was expressed as the minimal inhibitory concentration (MIC), the concentration at which no release of hemoglobin was observed after incubation. It was found that for the Lys/Leu diastereomer peptide 23 the MIC is 80 $\mu$M.

REFERENCES

1. Agawa, Y., Lee, S., Ono, S., Aoyagi, H., Ohno, M., Taniguchi, T., Anzai, K., and Kirino, Y. 1991. *J. Biol. Chem.* 266: 20218–20222.

2. Altenbach, C., and Hubbell, W. L. 1988. The aggregation state of spin-labeled melittin in solution and bound to phospholipid membranes: evidence that membrane-bound melittin is monomeric. *Proteins.* 3: 230–242.

3. Anderson, D., Terwilliger, T. C., Wickner, W., and Eisenberg, D. 1980. Melittin forms crystals which are suitable for high resolution X-ray structural analysis and which reveal a molecular 2-fold axis of symmetry. *J. Biol. Chem.* 255: 2578–2582.

4. Anzai, K., Hamasuna, M., Kadono, H., Lee, S., Aoyagi, H., and Kirino, Y. 1991. *Biochem. Biophys. Acta.* 1064: 256–266.

5. Bartlett, G. R. 1959. Phosphorus assay in column chromatography. *J Biol. Chem.* 234: 466–468.

6. Batenburg, A. M., Hibbeln, J. C., and de, K. B. 1987. Lipid specific penetration of melittin into phospholipid model membranes. *Biochim. Biophys. Acta.* 903: 155–165.

7. Batenburg, A. M., van, E. J., and de, K. B. 1988. Melittin-induced changes of the macroscopic structure of phosphatidylethanolamines. *Biochemistry.* 27: 2324–2331.

8. Batenburg, A. M., van, E. J., Leunissen, B. J., Verkleij, A. J., and de, K. B. 1987. Interaction of melittin with negatively charged phospholipids: consequences for lipid organization. *Febs Lett.* 223: 148–154.

9. Bazzo, R., Tappin, M. J., Pastore, A., Harvey, T. S., Carver, J. A., and Campbell, I. D. 1988. The structure of melittin. A 1H-NMR study in methanol. *Eur. J Biochem.* 173: 139–146.

10. Benkirane, N., Friede, M., Guichard, G., Briand, J. P., Van, R. M., and Muller, S. 1993. *J. Biol. Chem.* 268: 26279–26285.

11. Beschiaschvili, G., and Seelig, J. 1990. Melittin binding to mixed phosphatidylglycerol/phosphatidylcholine membranes. *Biochemistry.* 29: 52–58.

12. Bessalle, R., Kapitkovsky, A., Goria, A., Shalit, I. and Fridkin, M. 1990. *Febs Lett.* 274:151–155.

13. Bolen, E. J., and Holloway, P. W. 1990. Quenching of tryptophan fluorescence by brominated phospholipid. *Biochemistry.* 29: 9638–9643.

14. Boman, H. G. 1995. Peptide antibiotics and their role in innate immujnity. *Annu. Rev. Immun.* 13: 61–92.

15. Chen, H. C., Brown, J. H., Morell, J. L., and Huang, C. M. 1988. Synthetic magainin analogues with improved antimicrobial activity. *Febs Lett.* 236: 462–466.

16. Comut, I., Buttner, K., Dasseux, J. L., and Dufourcq, J. 1994. The amphipathic alpha-helix concept. Application to the de novo design of ideally amphipathic Leu, Lys peptides with hemolytic activity higher than that of melittin. *Febs Lett.* 349: 29–33.

17. Dempsey, C. E. 1990. The actions of melittin on membranes. *Biochim. Biophys. Acta.* 1031: 143–161.

18. Dhople, V. M., and Nagaraj, R. 1993. d-toxin, unlike melittin, has only hemolytic activity and no antimicrobial activity: rationalization of this specific biological activity. *Biosci. Rep.* 13: 245–250.

19. Eisenberg, D., Schwarz, E., Komaromy, M., and Wall, R. 1984. Analysis of membrane and surface protein sequences with the hydrophobic moment plot. *J. Mol. Biol.* 179: 125–142.

20. Fisher, P. J., Prendergast, F. G., Ehrhardt, M. R., Urbauer, J. L., Wand, A. J., Sedarous, S. S., M, c. D., and Buckley, P. J. 1994. *Nature.* 368: 651–653.

21. Gazit, E., Lee, W. J., Brey, P. T., and Shai, Y. 1994. *Biochemistry.* 33: 10681–10692.

22. Greenfield, N., and Fasman, G. D. 1969. Computed circular dichroism spectra for the evaluation of protein conformation. *Biochemistry.* 8: 4108–4116.

23. Habermann, E., and Jentsch, J. 1967. *Hoppe Seyler's Z. Physiol. Chem.* 348: 37–50.

24. Katchalski, E., and Sela, M. 1958. *Adv. Protein Chem.* 13: 243–492.

25. Kuchinka, E., and Seelig, J. 1989. Interaction of melittin with phosphatidylcholine membranes. Binding isotherm and lipid head-group conformation. *Biochemistry.* 28: 4216–4221.

26. Li, Z. Q., Merrifield, R. B., Boman, I. A., and Boman, H. G. 1988. Effects on electrophoretic mobility and antibacterial spectrum of removal of two residues from synthetic sarcotoxin IA and addition of the same residues to cecropin B. *FEBS Lett.* 231: 299–302.

27. Loew, L. M., Rosenberg, I.,-Bridge, M., and Gitler, C. 1983. Diffision potential cascade. Conventional detection of transferable membrane pores. *Biochemistry.* 22: 837–844.

28. Merrifield, R. B., Vizioli, L. D., and Boman, H. G. 1982. Synthesis of the antibacterial peptide cecropin A (1–33). *Biochemistry.* 21: 5020–5031.

29. Mor, A., Nguyen, V. H., Delfour, A., Migliore, S. D., and Nicolas, P. 1991. Isolation, amino acid sequence, and synthesis of dermaseptin, a novel antimicrobial peptide of amphibian skin. *Biochemistry.* 30: 8824–8830.

30. Okada, M., and Natori, S. 1984. Mode of action of a bactericidal protein induced in the haemolymph of Sarcophaga peregrina (flesh-fly) larvae. *Biochem. J.* 222: 119–124.

31. Oren, Z., and Shai, Y. 1996. A class of highly potent antibacterial peptides derived from pardaxin, a pore-forming peptide isolated from Moses sole fish Pardachirus marmoratus. *Eur. J. Biochem.* 237: 303–310.

32. Papahadjopoulos, D., and Miller, N. 1967. Phospholipid model membranes. Structural characteristics of hydrated liquid crystals. *Biochim. Biophys. Acta.* 135: 624–638.

33. Perez, P. E., Houghten, R. A., and Blondelle, S. E. 1994. Determination of the secondary structure of selected melittin analogues with different haemolytic activities. *Biochem. J.*

34. Pouny, Y., and Shai, Y., 1992. Interaction of D-amino acid incorporated analogues of pardaxin with membranes. *Biochemistry.* 39: 9482–9490.

35. Rapaport, D., and Shai, Y. 1992. Aggregation and organization of pardaxin in phospholipid membranes. A fluorescence energy transfer study. *J. Biol. Chem.* 267: 6502–6509.

36. Rapaport, D., and Shai, Y. 1991. Interaction of fluorescently labeled pardaxin and its analogues with lipid bilayers. *J. Biol. Chem.* 266: 23769–23775.

37. Rizzo, V., Stankowski, S., and Schwarz, G. 1987. Alamethicin incorporation in lipid bilayers: a thermodynamic study. *Biochemistry.* 26: 2751–9.

38. Russell, P. E., Milling, R. J., and Wright, K. 1995. Fifty years of antimicrobials: past perspectives and future trends (Hunter P. A., Darby G. K., and Russell N. I. Ed) pp. 67–85, Cambridge University Press, Cambridge.

39. Schwarz, G., Gerke, H., Rizzo, V., and Stankowski, S. 1987. Incorporation kinetics in a membrane, studied with the pore-formiing peptide alamethicin. *Biophys. J.* 52: 685–692.

40. Segrest, J. P., De, L. H., Dohlman, J. G., Brouillette, C. G., and Anantharamaiah, G. M. 1990. Amphipathic helix motif: classes and properties [published erratum appears in Proteins 1991;9(1):79]. *Proteins.* 8: 103–117.

41. Shai, Y. 1995. Molecular recognition between membrane-spanning helices. *TIBS*. in press.
42. Shai, Y. 1994. Pardaxin: channel formation by a shark repellant peptide from fish. *Toxicology*. 87: 109–129.
43. Shai, Y., Fox, J., Caratsch, C., Shih, Y. L., Edwards, C., and Laaarovici, P. 1988. Sequencing and synthesis of pardaxin, a polypeptide from the Red Sea Moses sole with ionophore activity. *FEBS Lett*. 242: 161–166.
44. Shai, Y., Fox, J., Caratsch, C., Shih, Y. L., Edwards, C., and Lazarovici, P. 1988. Sequencing and synthesis of pardaxin, a polypeptide from the Red Sea Moses sole with ionophore activity. *FEBS Lett*. 242: 161–166.
45. Shai, Y., Hadari, Y. R., and Finkels, A. 1991. pH-dependent pore formation properties of pardaxin analogues. *J. Biol. Chem.* 266: 22346–22354.
46. Shaw, N. 1974. Lipid composition as a guide to the classification of bacteria. *Adv. Appl. Microbiol.* 17: 63–108.
47. Sims, P. J., Waggoner, A. S., Wang, C. H., and Hoffmann, J. R. 1974. Studies on the mechanism by cyanine dyes measure membrane potential in red blood cells and phosphatidylcholine vesicles. *Biochemistry*. 13: 3315–3330.
48. Steiner, H., Hultmark, D., Engstrom, A., Bennich, H., and Boman, H. G. 1981. Sequence and specificity of two antibacterial proteins involved in insect immunity. *Nature*. 292: 246–248.
49. Terwilliger, T. C., and Eisenberg, D. 1982. The structure of melittin. I. Structure determination and partial refinement. *J. Biol. Chem.* 257: 6010–6015.
50. Terwilliger, T. C., and Eisenberg, D. 1982. The structure of melittin. II. Interpretation of the structure. *J. Biol. Chem.* 257: 6016–6022.
51. Thompson, S. A., Tachibana, K., Nakanishi, K., and Kubota, 1. 1986. Melittin-Like Peptides from the Shark-Repelling Defense Secretion of the Sole *Pardachirus pavoninus*. *Science*. 233: 341–343.
52. Verkleij, A. J., Zwaal, R. F., Roelofsen, B., Coinfirius, P., Kastelijn, D., and Deenen, L. v. 1973. The asymmetric distribution of phospholipids in the human red cell membrane. A combined study using phospholipases and freeze-etch electron microscopy. *Biochim. Biophys. Acta*. 323: 178–193.
53. Wade, D., Boman, A., Wahlin, B., Drain, C. M., Andreu, D., Boman, H. G., and Merrifield, R. B. 1990. *Proc. Natl. Acad. Sci. USA*. 87: 4761–4765.
54. Wu, C. S., Ikeda, K., and Yang, J. T. 1981. Ordered conformation of polypeptides and proteins in acidic dodecyl sulfate solution. *Biochemistry*. 20: 566–570.
55. Zagorski, M. G., Norman, D. G., Barrow, C. 3., Iwashita, T., Tachibana, K., and Patel, D. J. 1991. Solution structure of pardaxin P-2. *Biochemistry*. 30: 8009–8017.

What is claimed is:

1. A peptide having a selective cytolytic activity manifested in that it has a cytolytic activity on pathogenic cells, and it has no cytolytic effect on red blood cells or has a cytolytic effect on red blood cells at concentrations which are substantially higher than that in which it manifests said cytolytic activity on pathogenic cells, said peptide having the following characteristics:
   (a) it is a peptide comprising both L-amino acid residues and D-amino acid residues;
   (b) the peptide has a net positive charge which is greater than +1; and
   (c) the peptide is amphipathic, with the proviso that said peptide is not D-L$^5$,L$^{19}$-TA$_2$-Par.
2. The peptide according to claim 1, having a selective cytolytic activity on pathogenic cells, the selectivity being manifested in that the peptide induces cytolysis of the pathogenic cells at a much lower concentration than that in which it induces cytolysis of normal, non-pathogenic cells.

3. The peptide according to claim 1, possessing a cytolytic acvity against bacteria, virus, fungi, protozoa on mycoplasma.

4. The peptide according to claim 3 having a cytolytic activity against bacteria.

5. The peptide according to claim 1, comprising both D- and L-amino acid residues having a sequence such that a homogeneous peptide comprsing only L- or only D-amino acid residues and having the same amino acid sequence as said peptide, has an α-helix configuration and has a broad spectrum cytolytic activity manifested on a variety of cells.

6. The peptide according to claim 1, which is a diastereomer derived from pardaxin or from a fragment thereof.

7. The peptide according to claim 6, in which the net positive charge greater than +1 is due to the native amino acid composition of said pardaxin or fragment thereof, or is attained by neutralization of free carboxyl groups thereof, or by the addition of positively charged groups thereto.

8. The peptide according to claim 7, which is selected from a diastereomer of pardaxin or of a fragment thereof to which Lys residues have been added to the N-terminus and/or aminoethylamino groups having been added to the C-terminus.

9. The peptide according to claim 1 which is a diastereomer derived from melittin or from fragments thereof.

10. A pharmaceutical composition comprising a non-hemolytic cytolytic peptide according to claim 1, and a pharmaceutical acceptable carrier.

11. The pharmaceutical composition according to claim 10, for use in the treatment of infections caused by pathogenic organisms.

12. The pharmaceutical composition according to claim 11, wherein the pathogenic organism is selected from the group consisting of bacteria, fungi, protozoa, and mycoplasma.

13. The pharmaceutical composition according to claim 10, for use in the treatment of cancer.

14. A peptide selected from the group consisting of peptides of the sequence:

Gly-Phe-Phe-Ala-Leu-Ile-Pro-Lys-Ile-Ile-Ser-Ser-Pro-Leu-Phe-Lys-Thr-Leu-Leu-Ser-Ala-Val-Gly-Ser-Ala-Leu-Ser-Ser-Ser-Gly-Gly-Gln-Glu-(NH—$CH_2$—$CH_2$—$NH_2$)$_2$,

Gly-Phe-Phe-Ala-Leu-Ile-Pro-Lys-Ile-Ile-Ser-Ser-Pro-Leu-Phe-Lys-Thr-Leu-Leu-Ser-Ala-Val-NH—$CH_2$—$CH_2$—$NH_2$,

Gly-Phe-Phe-Ala-Leu-Ile-Pro-Lys-Ile-Ile-Ser-Ser-Pro-Leu-Phe-Lys-Thr-Leu-Leu-Ser-Ala-Val,

Lys-Gly-Phe-Phe-Ala-Leu-Ile-Pro-Lys-Ile-Ile-Ser-Ser-Pro-Leu-Phe-Lys-Thr-Leu-Leu-Ser-Ala-Val-NH—$CH_2$—$CH_2$—$NH_2$,

Lys-Lys-Gly-Phe-Phe-Ala-Leu-Ile-Pro-Lys-Ile-Ile-Ser-Ser-Pro-Leu-Phe-Lys-Thr-Leu-Leu-Ser-Ala-Val-NH—$CH_2$—$CH_2$—$NH_2$,

Lys-Lys-Gly-Phe-Phe-Ala-Leu-Ile-Pro-Lys-Ile-Ile-Ser-Ser-Pro-Leu-Phe-Lys-Thr-Leu-Leu-Ser-Ala-Val,

Gly-Phe-Phe-Ala-Leu-Ile-Pro-Lys-Ile-Ile-Ser-NH—$CH_2$—$CH_2$—$NH_2$

Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-$NH_2$,

Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-COOH,

Gly-Ile-Gly-Ala-Val-Leu-Lys-Val-Leu-Thr-Thr-Gly-Leu-Pro-Ala-Leu-Ile-Ser-Trp-Ile-Lys-Arg-NH—$CH_2$—$CH_2$—$NH_2$,

Ala-Val-Leu-Lys-Val-Leu-Thr-Thr-Gly-Leu-Pro-Ala-Leu-Ile-Ser-Trp-Ile-Lys-Arg-NH—$CH_2$—$CH_2$—$NH_2$, and Lys-Leu-Leu-Leu-Lys-Leu-Leu-Leu-Lys-Leu-Leu-Lys-$NH_2$.

15. The peptide according to claim 9, in which the net positive charge greater than +1 is due to the native amino acid composition of said melittin or fragment thereof, or is attained by neutralization of free carboxyl groups thereof, or by the addition of positively charged groups thereto.

* * * * *